United States Patent
Yun et al.

(10) Patent No.: US 9,481,828 B2
(45) Date of Patent: **\*Nov. 1, 2016**

(54) LIQUID CRYSTAL COMPOUND CONTAINING CYCLOBUTYL GROUP AND DIFLUOROMETHYLENEOXY LINKING GROUP, AND PREPARATION METHOD AND USE THEREOF

(71) Applicant: ShijiaZhuang Chengzhi Yonghua Display Materials Co., Ltd., Hebei Province (CN)

(72) Inventors: Guoliang Yun, Hebei Province (CN); Ruimao Hua, Hebei Province (CN); Kui Wang, Hebei Province (CN); Wenhai Lv, Hebei Province (CN); Jian Wang, Hebei Province (CN); Yaohua Han, Hebei Province (CN); Yunxia Qiao, Hebei Province (CN)

(73) Assignee: Shijiazhuang Chengzhi Yonghua Display Material Co., Ltd., Shi Jia Zhuang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,271

(22) PCT Filed: Nov. 26, 2013

(86) PCT No.: PCT/CN2013/001450
§ 371 (c)(1),
(2) Date: Dec. 11, 2014

(87) PCT Pub. No.: WO2014/089903
PCT Pub. Date: Jun. 19, 2014

(65) Prior Publication Data
US 2015/0284632 A1    Oct. 8, 2015

(30) Foreign Application Priority Data

Dec. 14, 2012 (CN) ............................ 2012 1 0545321

(51) Int. Cl.
*C07C 43/21* (2006.01)
*C07C 43/225* (2006.01)
(Continued)

(52) U.S. Cl.
CPC ........... *C09K 19/3066* (2013.01); *C07C 43/21* (2013.01); *C07C 43/225* (2013.01);
(Continued)

(58) Field of Classification Search
None
See application file for complete search history.

(56) References Cited

U.S. PATENT DOCUMENTS

| 9,028,714 B2 * | 5/2015 | Xu | C09K 19/3402 |
| | | | 252/299.61 |
| 2014/0312276 A1 * | 10/2014 | Lu | C09K 19/3068 |
| | | | 252/299.63 |

FOREIGN PATENT DOCUMENTS

| CN | 102675062 | 9/2012 |
| CN | 102924243 | 2/2013 |

(Continued)

OTHER PUBLICATIONS

English Translation of CN103361078.*
(Continued)

*Primary Examiner* — Cynthia H Kelly
*Assistant Examiner* — Anna Malloy
(74) *Attorney, Agent, or Firm* — Blank Rome LLP

(57) ABSTRACT

A liquid crystal compound containing cyclobutyl and a linking group difluoromethyleneoxy, and a preparation method and use thereof are disclosed. The compound is as shown in Formula I. The liquid crystal compound containing cyclobutyl as a terminal group and difluoromethyleneoxy (—CF$_2$O—) as a linking group in the molecular structure of Formula I according to the present invention, has not only a high dielectric anisotropy, but also importantly an extremely fast response speed and a high clearing point, which are of great significance for the formulation of a liquid crystal mixture.

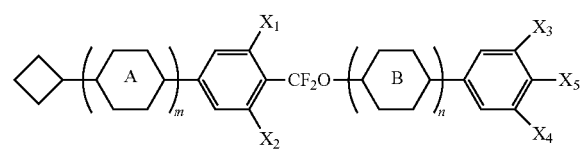

10 Claims, 1 Drawing Sheet

(51) Int. Cl.
*C07D 309/06* (2006.01)
*C09K 19/34* (2006.01)
*C09K 19/30* (2006.01)
*C09K 19/44* (2006.01)
*C07C 43/29* (2006.01)
*C09K 19/04* (2006.01)
*C09K 19/12* (2006.01)

(52) U.S. Cl.
CPC ............ *C07C 43/29* (2013.01); *C07D 309/06* (2013.01); *C09K 19/44* (2013.01); *C07C 2101/04* (2013.01); *C07C 2101/14* (2013.01); *C09K 2019/0466* (2013.01); *C09K 2019/123* (2013.01); *C09K 2019/301* (2013.01); *C09K 2019/3004* (2013.01); *C09K 2019/3019* (2013.01); *C09K 2019/3096* (2013.01); *C09K 2019/3422* (2013.01)

(56) References Cited

FOREIGN PATENT DOCUMENTS

| CN | 102964226 | | | 3/2013 |
|---|---|---|---|---|
| CN | 103254911 | | | 8/2013 |
| CN | 103254911 | A | * | 8/2013 |
| CN | 103254912 | | | 8/2013 |
| CN | 103254912 | A | * | 8/2013 |
| CN | 103275735 | | | 9/2013 |
| CN | 103275735 | A | * | 9/2013 |
| CN | 103289707 | | | 9/2013 |
| CN | 103289707 | A | * | 9/2013 |
| CN | 103305229 | | | 9/2013 |
| CN | 103305229 | A | * | 9/2013 |
| CN | 103305231 | | | 9/2013 |
| CN | 103305231 | A | * | 9/2013 |
| CN | 103305232 | | | 9/2013 |
| CN | 103305232 | A | * | 9/2013 |
| CN | 103320145 | | | 9/2013 |
| CN | 103320145 | A | * | 9/2013 |
| CN | 103333700 | | | 10/2013 |
| CN | 103333700 | A | * | 10/2013 |
| CN | 103351877 | | | 10/2013 |
| CN | 103351877 | A | * | 10/2013 |
| CN | 103361078 | | | 10/2013 |
| CN | 103361078 | A | * | 10/2013 |

OTHER PUBLICATIONS

English Translation of CN103351877.*
English Translation of CN103333700.*
English Translation of CN103320145.*
English Translation of CN103305231.*
English Translation of CN103305232.*
English Translation of CN103305229.*
English Translation of CN103289707.*
English Translation of CN103275735.*
English Translation of CN103254912.*
English Translation of CN103254911.*
International Search Report dated Jan. 22, 2014; International Application No. PCT/CN2013/001450; International Filing Date: Nov. 26, 2013; 5 pages.
English translation dated Jan. 22, 2014; International Search Report; International Application No. PCT/CN2013/001450; International Filing Date: Nov. 26, 2013; 4 pgs.
English abstract; Chinese Application No. CN103361078; 1 page. Jul. 29, 2016.
English abstract; Chinese Application No. CN103351877; 1 page. Jul. 29, 2016.
English abstract; Chinese Application No. CN103333700; 1 page. Jul. 29, 2016.
English abstract; Chinese Application No. CN103320145; 1 page. Jul. 29, 2016.
English abstract; Chinese Application No. CN103305231; 1 page. Jul. 29, 2016.
English abstract; Chinese Application No. CN103305232; 1 page. Jul. 29, 2016.
English abstract; Chinese Application No. CN103305229; 1 page. Jul. 29, 2016.
English abstract; Chinese Application No. CN103289707; 1 page. Jul. 29, 2016.
English abstract; Chinese Application No. CN103275735; 1 page. Jul. 29, 2016.
English abstract; Chinese Application No. CN103254912; 1 page. Jul. 29, 2016.
English abstract; Chinese Application No. CN103254911; 1 page. Jul. 29, 2016.
English abstract; Chinese Application No. CN102964226; 1 page. Jul. 29, 2016.
English abstract; Chinese Application No. CN102924243; 1 page. Jul. 29, 2016.
English abstract; Chinese Application No. CN102675062; 1 page. Jul. 29, 2016.

* cited by examiner

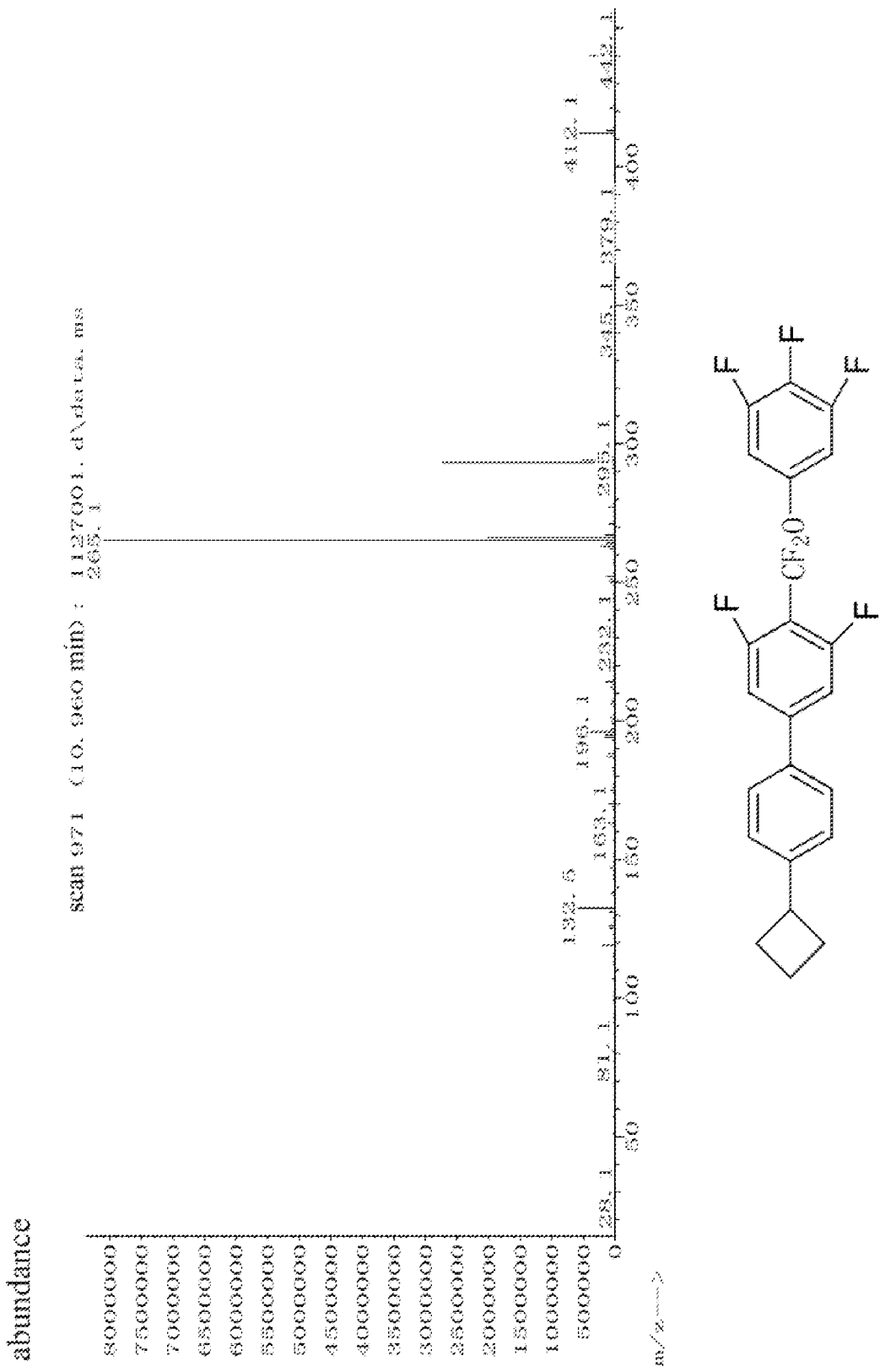

LIQUID CRYSTAL COMPOUND CONTAINING CYCLOBUTYL GROUP AND DIFLUOROMETHYLENEOXY LINKING GROUP, AND PREPARATION METHOD AND USE THEREOF

FIELD OF THE INVENTION

The present invention relates to the field of liquid crystal compounds and use thereof and more particularly, to a liquid crystal compound containing cyclobutyl and a linking group difluoromethyleneoxy, and preparation method and use thereof.

BACKGROUND OF THE INVENTION

At present, the application range of liquid crystal compounds become increasingly widened, including their application in various types of displays, electro-optical devices, sensors and so on. There are numerous species of liquid crystal compounds that are used in the field of display. Among them, nematic liquid crystals are most widely used, and for example, they have been used in passive matrix-type TN, STN matrix display and a system having TFT active matrix.

The thin film transistor liquid crystal display (TFT-LCD) has an enormous market and gradually become mature in recent years. However, the requirements on display technologies are continuously increased, especially in terms of realizing the fast response, and decreasing the driving voltage to lower the power consumption. As one of optoelectronic materials important for the liquid crystal display, the liquid crystal material plays an important role in improvement of the performances of the liquid crystal display.

The liquid crystal materials need to have good chemical and thermal stabilities, and have stabilities to electric and electromagnetic radiation. However, in addition to these, the liquid crystal materials used in TFT-LCD also should have a wide temperature range of the nematic phase, a suitable birefringence anisotropy, an extremely high resistivity, a good anti-UV performance, a high charge retention, a low vapor pressure, and so on.

For dynamic image display application, for example, liquid crystal display television, the liquid crystal is required to have a quite fast response speed and thus a low rotary viscosity $\gamma 1$, in order to achieve high quality display and eliminate image ghosting and trailing. Furthermore, in order to lower the energy consumption of the device, the driving voltage of the liquid crystal is expected to be as low as possible. Accordingly, increase of the dielectric anisotropy $\Delta \in$ of the liquid crystal is of great importance for mixed liquid crystals.

Numerous studies show that once a linking group difluoromethyleneoxy ($-CF_2O-$) is introduced in a liquid crystal, the rotary viscosity $\gamma_1$ of the liquid crystal would be lowered. Moreover, due to the contribution of the difluoromethyleneoxy bridge ($-CF_2O-$) to dipole moment, the dipole moment of fluorine atom in the terminal group is improved to some degree, so that the dielectric anisotropy $\Delta \in$ of the liquid crystal molecule is increased. Merk of Germany and Chisso Corporation of Japanese have disclosed some liquid crystal compounds having difluoromethyleneoxy ($-CF_2O-$) as a linking group and substituted with different groups (e.g. CN1717468A, CN101143808A, and CN101157862A etc). However, the introduction of the group $-CF_2O-$ will greatly lower the clearing point of the liquid crystal. The decrease in the clearing point caused by the group $-CF_2O-$ needs to be compensated by adding compounds having a high viscosity and a high clearing point in the formulation of a liquid crystal mixture, which restricts the increase space in response speed of the liquid crystal mixture.

As a core functional material in liquid crystal display devices, the liquid crystal material is required to have a wide range of performance parameters, in order to meet the requirements of various performance parameters imposed by the liquid crystal display device, and accommodate for the process requirements of the liquid crystal display device. However, any single one of monomer liquid crystal materials cannot meet all of the requirements, and thus it is expected to synthesize monomer liquid crystals having distinct performances, in order to meet the property requirements of the LCD device through formulation and mixing.

SUMMARY OF THE INVENTION

An objective of the present invention is to provide a liquid crystal compound containing cyclobutyl and a linking group difluoromethyleneoxy, and preparation method and use thereof.

BRIEF DESCRIPTION OF THE DRAWINGS

FIG. 1 is a mass spectrum of the product prepared in Example 1.

DETAILED DESCRIPTION OF THE INVENTION

The liquid crystal compound containing cyclobutyl and a linking group difluoromethyleneoxy according to the present invention has a general structural formula as shown in Formula I:

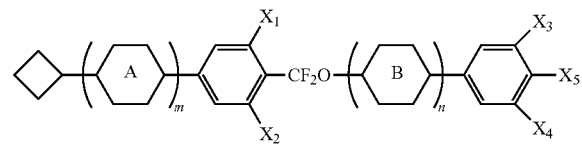

Formula I where,

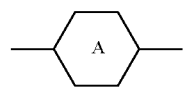

is selected from at least one of 1,4-cyclohexylene, 1,4-cyclohexylene in which one $-CH_2-$ is substituted with O, 1,4-phenylene and 1,4-phenylene substituted with fluoro;

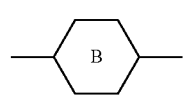

is selected from at least one of 1,4-phenylene and 1,4-phenylene substituted with fluoro;

$X_1$, $X_2$, $X_3$ and $X_4$ are each independently selected from any one of H and F;
$X_5$ is selected from any one of H, F, Cl, $CF_3$, $CHF_2$, $OCF_3$ and $OCHF_2$;
m is selected from 1 or 2 or 3, and
n is selected from 0 or 1.
Specifically, the compound of Formula I is any one of the compounds of Formulas I1 to I18:
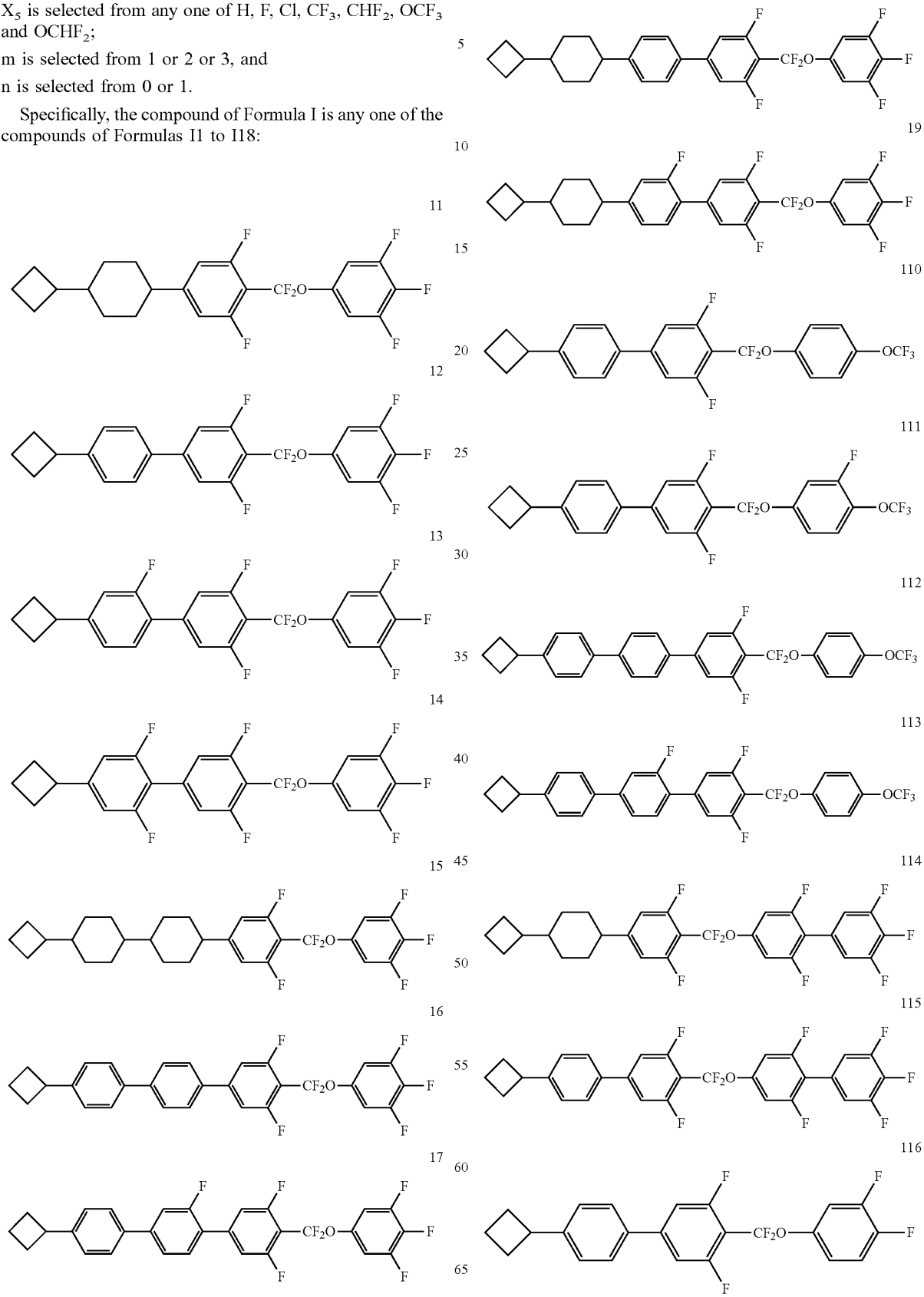

-continued

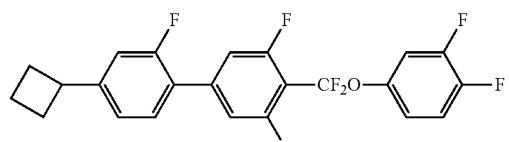
117

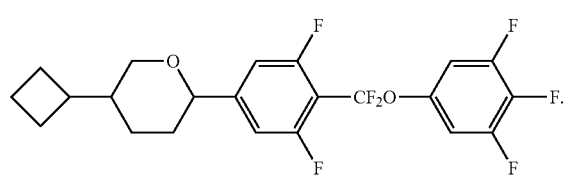
118

The compound of Formula I has varying performances depending on ring A, m, $X_1$, $X_2$, $X_3$, $X_4$, and $X_5$, thus having a wide application range. The compound of Formula I may be used as a base material of a liquid crystal mixture, or added as additive to a base liquid crystal material composed of other types of compounds, for example, to improve the dielectric anisotropy $\Delta\epsilon$ or/and rotary viscosity $\gamma_1$ or/and threshold voltage $V_{th}$ or/and contrast at low temperature or/and optical anisotropy $\Delta n$ or/and clearing point Cp of the liquid crystal mixture.

Pure compound of Formula I is colorless, and exhibits high stabilities to light, heat, and chemicals. Particularly, the compound of Formula I exhibits a large dielectric anisotropy $\Delta\epsilon$, and good performances such as response speed and contrast at low temperature, as well as the advantage of inhibiting the formation of a smectic phase, suggesting that a liquid crystal mixture with the compound of Formula I will have a good storage stability at low temperature. Therefore, liquid crystal mixtures containing a component A (namely, at least one of the compounds of Formula I according to the present invention) also fall within the protection scope of the present invention.

Specifically, the liquid crystal mixture is consisted of the component A, a component B and a component C.

The component B comprises at least one of the compounds of Formula II, and preferably one or two of the compounds of Formula II.

The component C comprises at least one of the compounds of Formula III, and preferably three to ten of the compounds of Formula III.

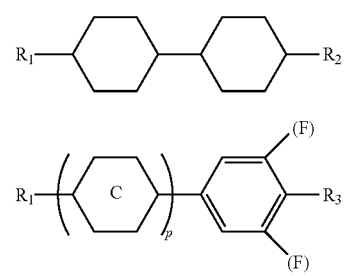

In Formulas II and III, $R_1$ and $R_2$ are each selected from C1-C6 alkyl or C2-C6 alkenyl;

$R_3$ is hydrogen, fluoro or C1-C6 alkyl;

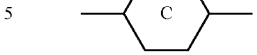

is selected from at least one of 1,4-cyclohexylene, 1,4-phenylene and 1,4-phenylene substituted with fluoro;
p is 2 or 3;
(F) represents H or F; and
in $R_1$, $R_2$ and $R_3$, C1-C6 alkyl is specifically C1-C5 alkyl, C1-C4 alkyl, C1-C3 alkyl, C1-C2 alkyl, C2-C5 alkyl, C2-C4 alkyl, C2-C3 alkyl, C3-C5 alkyl, C3-C4 alkyl or C4-C5 alkyl, and more specifically —$C_2H_5$, —$C_4H_9$, —$C_3H_7$ or —$CH_3$; and
C2-C6 alkenyl is specifically C2-C5 alkenyl, C2-C4 alkenyl, C2-C3 alkenyl, C3-C5 alkyl, C3-C4 alkenyl, or C4-C5 alkenyl, and more specifically —$C_2H_5$, —$C_4H_9$, —$C_3H_9$, or —$CH_3$.

The weight ratio of the component A, component B and component C is 1-40:5-40:5-80, preferably 10-35:15-35:25-75, more preferably 5-10:25:75, and specifically 5:25:75 or 10:25:75.

The compound of formula II is preferably any one of the compounds having a structural formula below:

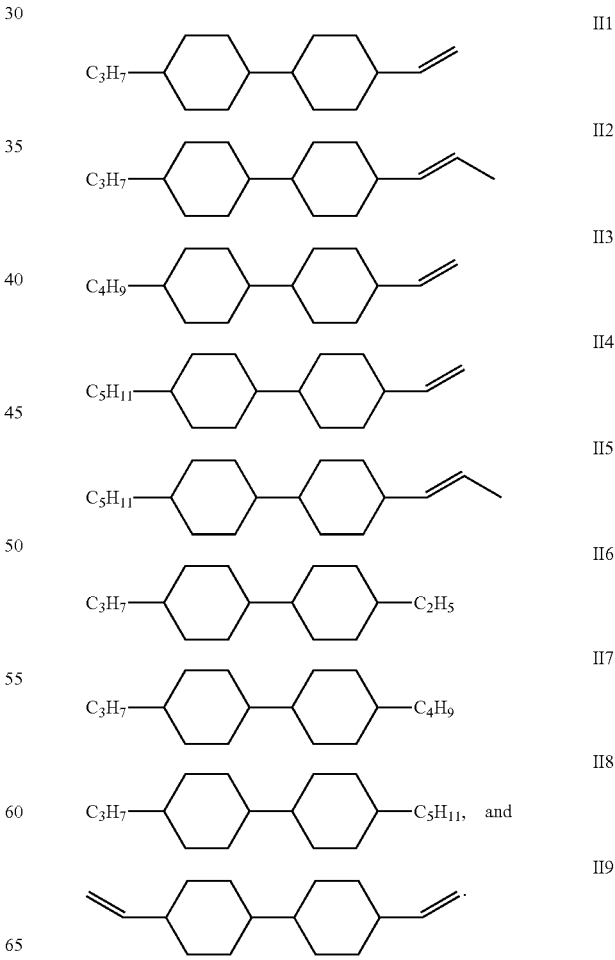

The compound of Formula III is preferably any one of the compounds having structural formulas III1 to III8 below:

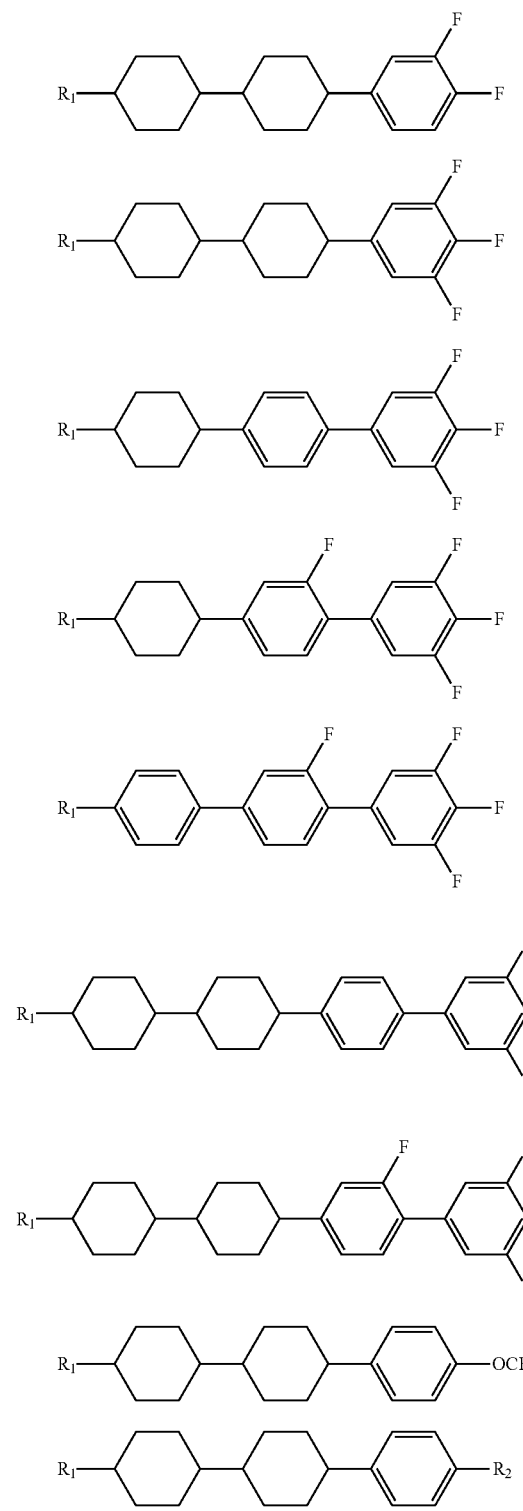

In Formulas III1 to III9, $R_1$ is selected from at least one of C1-C6 alkyl and C2-C6 alkenyl.

In the component B, the compounds of Formula II are each present in an amount of 10-25%, and specifically 23%, 24%, or 23-24% by weight of the total weight of the liquid crystal mixture. In the component C, the compounds of Formula III are each present in an amount of 2-12%, and specifically 2%, 5%, 6%, 7%, 8%, 10%, 2-10%, 2-7%, 2-S %, 5-10%, 5-7%, 7-10%, 2-8%, 6-10% or 2-6% by weight of the total weight of the liquid crystal mixture.

The liquid crystal mixture may further comprise at least one of an anti-oxidant, an anti-UV agent and a chiral agent.

The liquid crystal mixture is specifically a liquid crystal mixture a, b, c or d below.

The liquid crystal mixture a comprises or is consisted of in parts by weight:

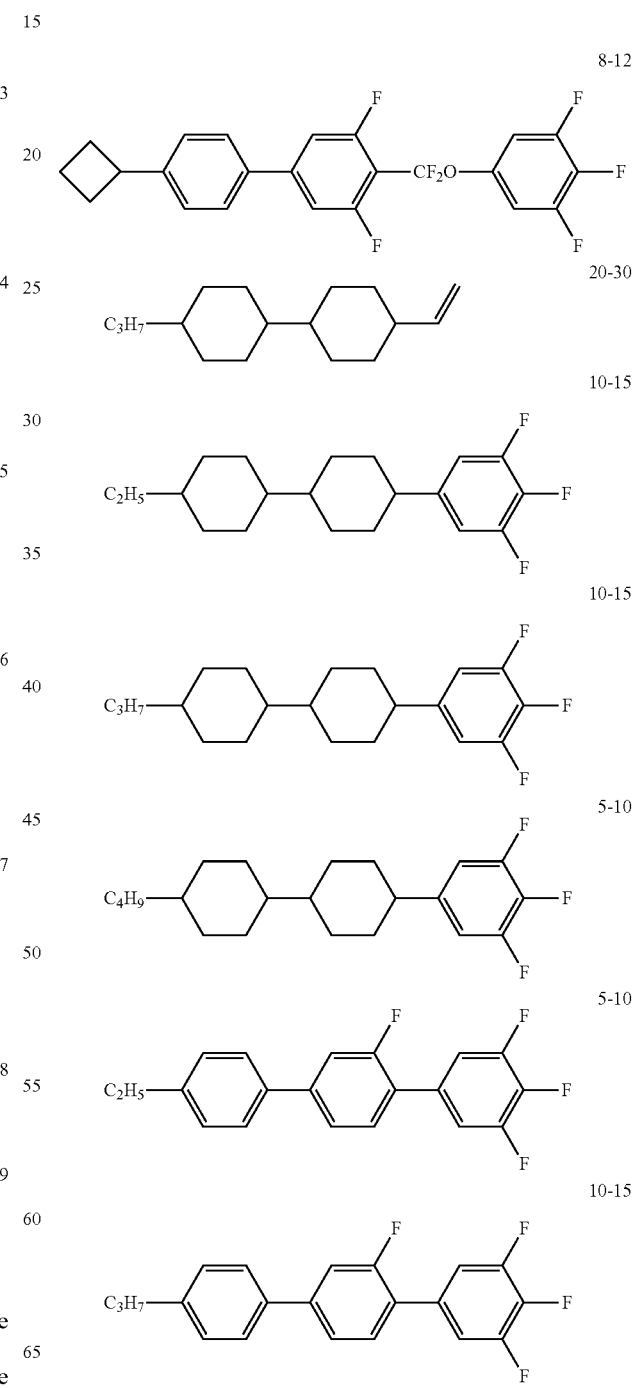

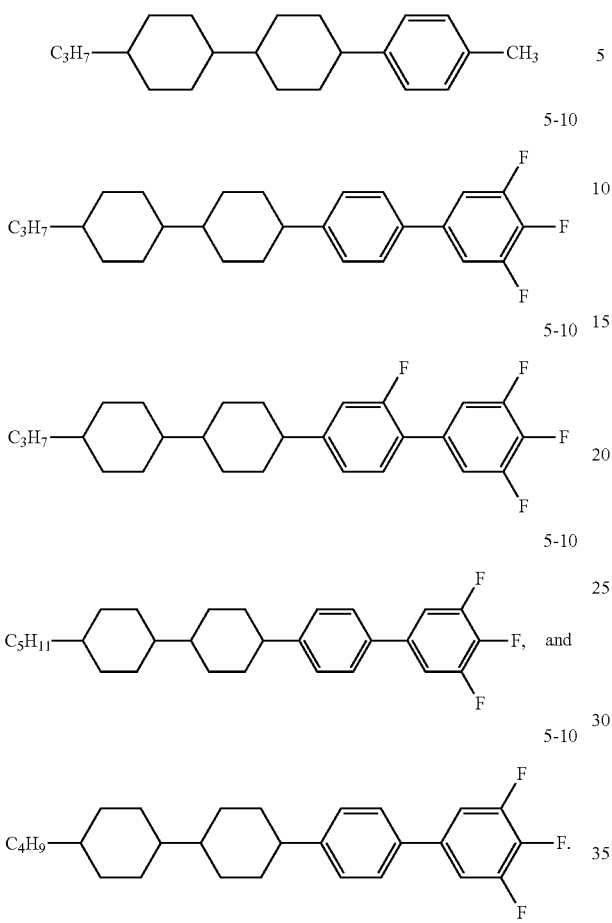
The liquid crystal mixture a specifically comprises, or is consisted of, in parts by weight:
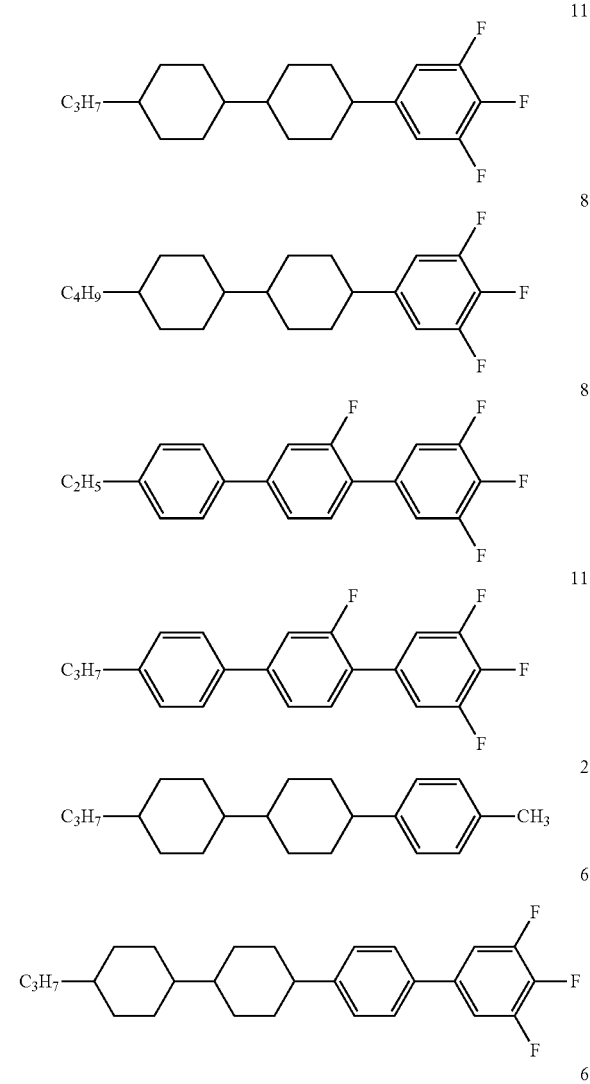

The liquid crystal mixture b comprises, or is consisted of, in parts by weight:
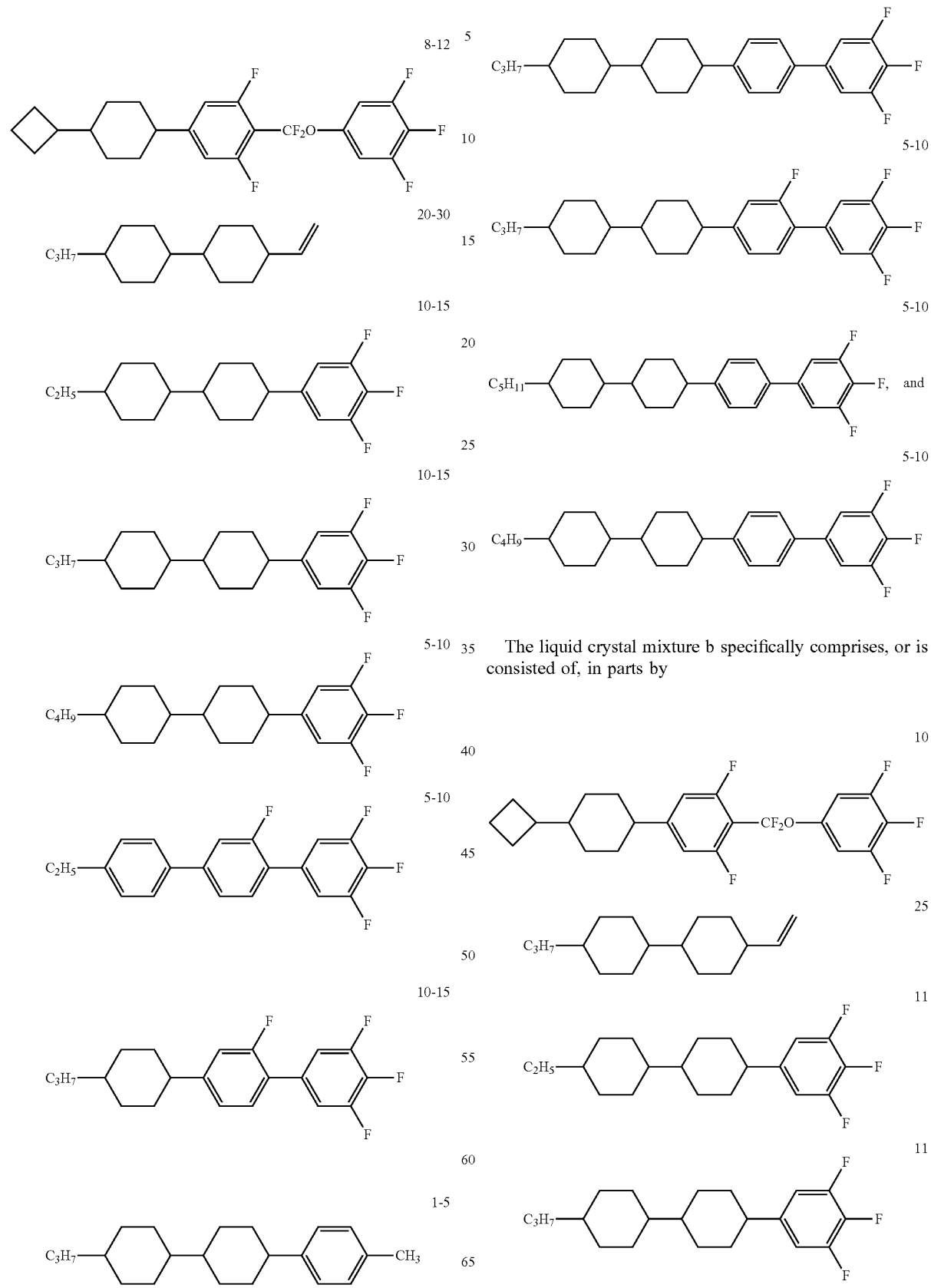
The liquid crystal mixture b specifically comprises, or is consisted of, in parts by -continued
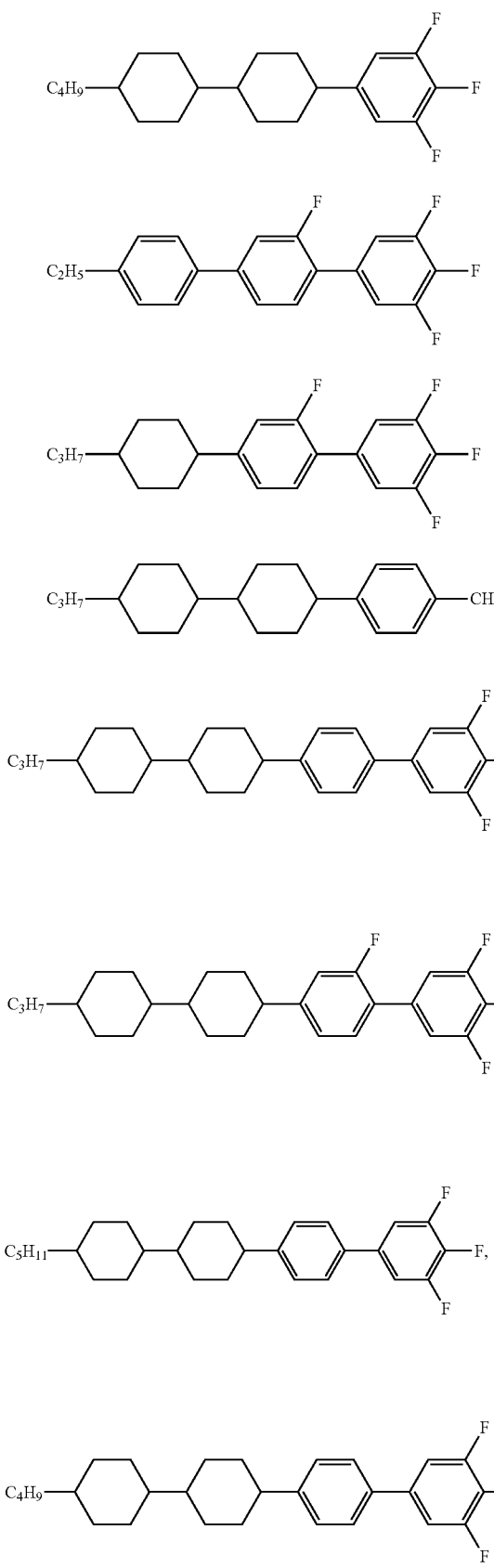
The liquid crystal mixture c comprises, or is consisted of, in parts by weight:
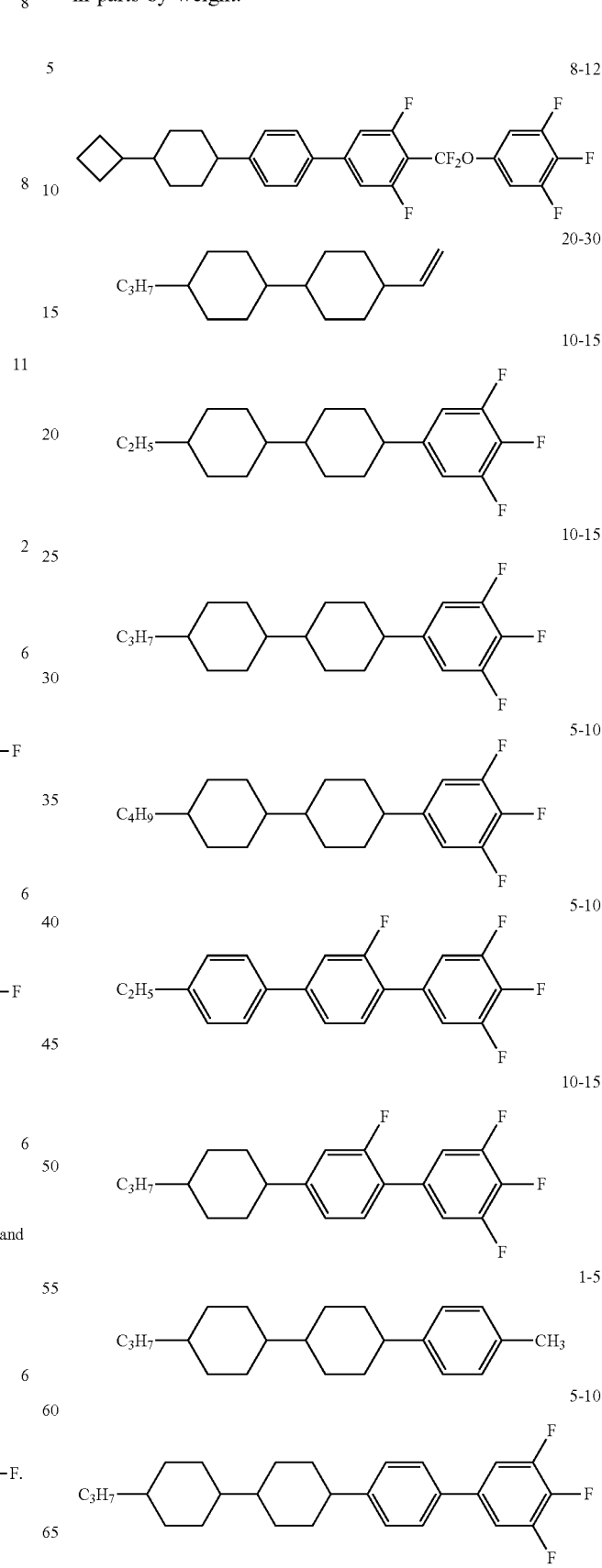

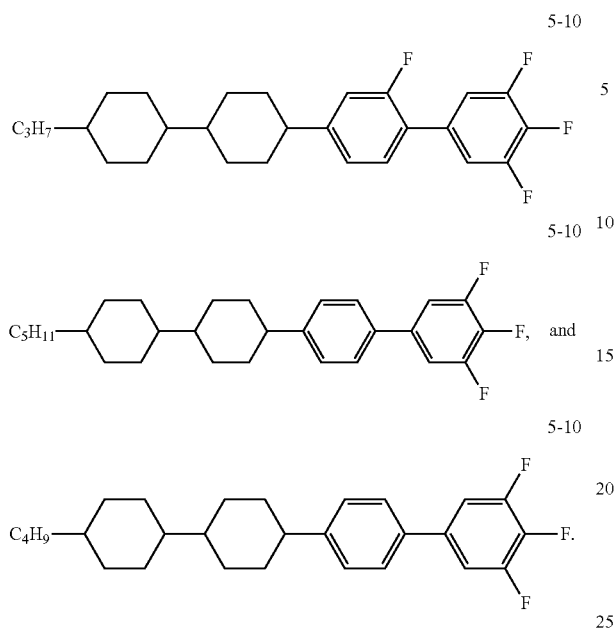
The liquid crystal mixture c specifically comprises, or is consisted oft in parts by weight:
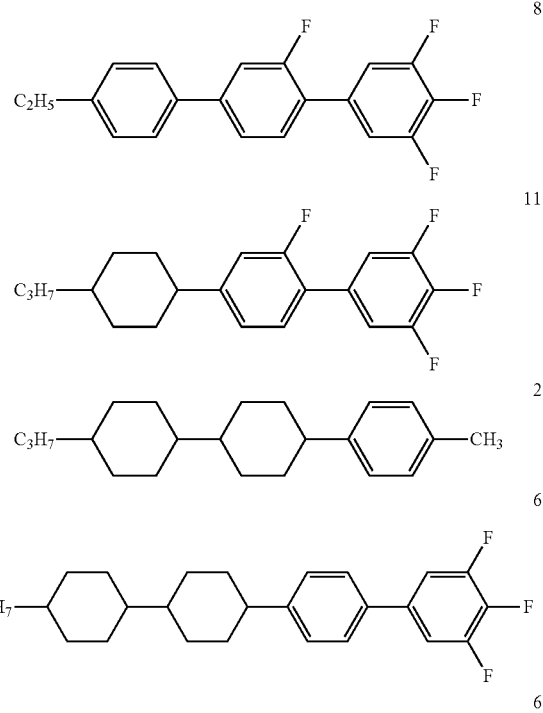
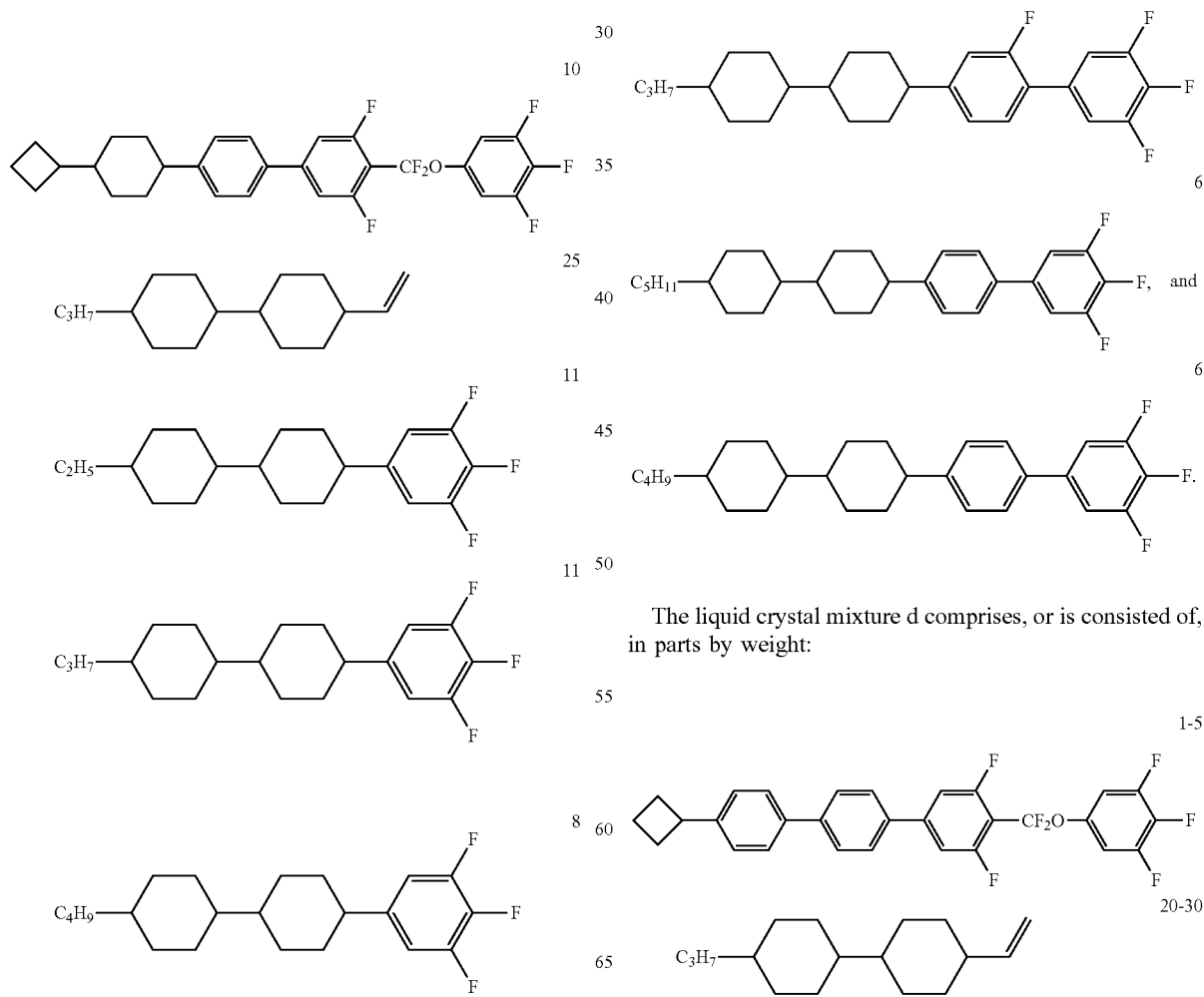
The liquid crystal mixture d comprises, or is consisted of, in parts by weight:

10-15
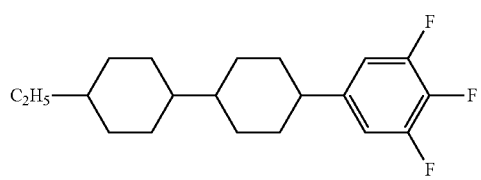
10-15
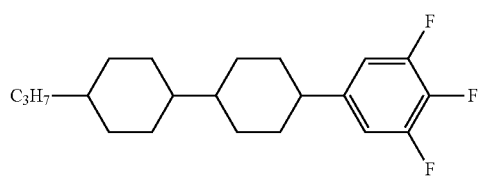
5-10
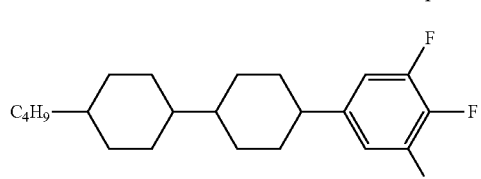
5-10
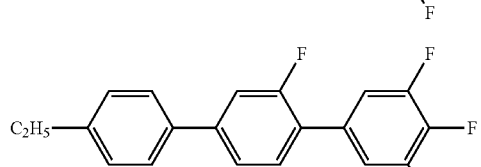
10-15
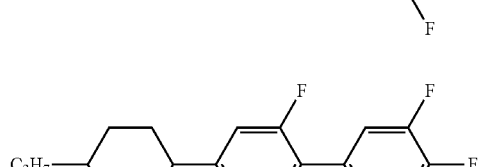
1-5
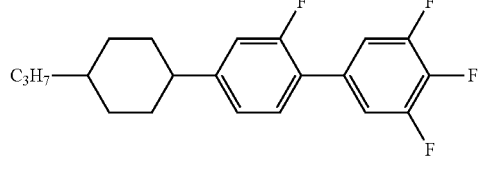
5-10
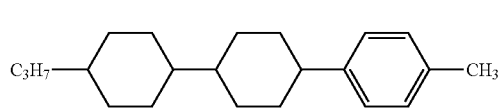
5-10
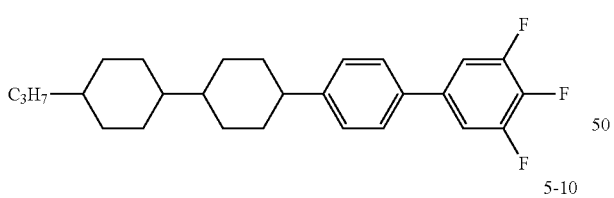
5-10
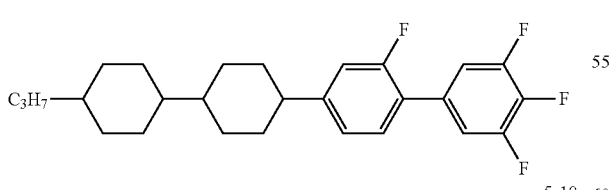, and
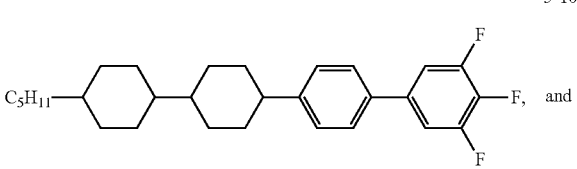
5-10
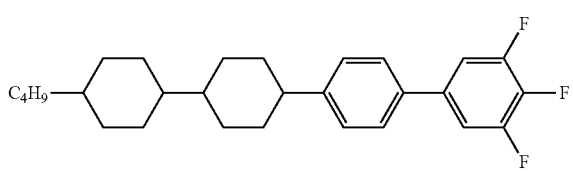
The liquid crystal mixture d specifically comprises, or is consisted of, in parts by weight:
5
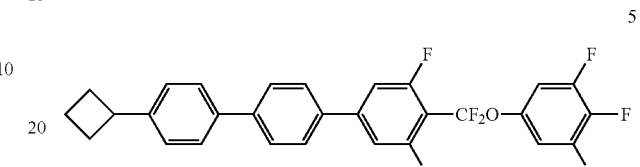
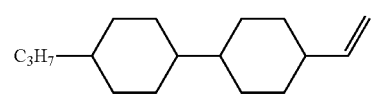
11
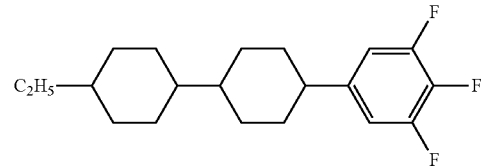
11
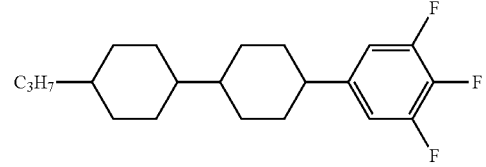
8
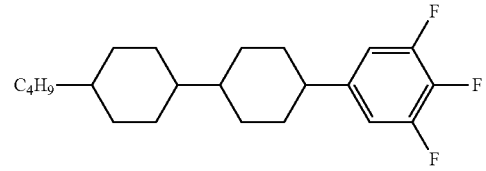
8
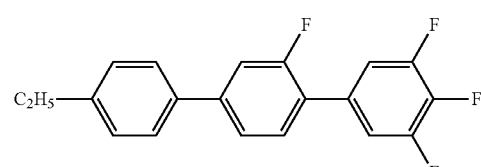
11
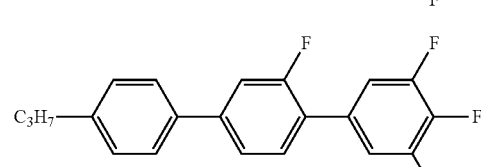
2
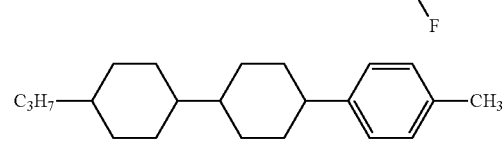

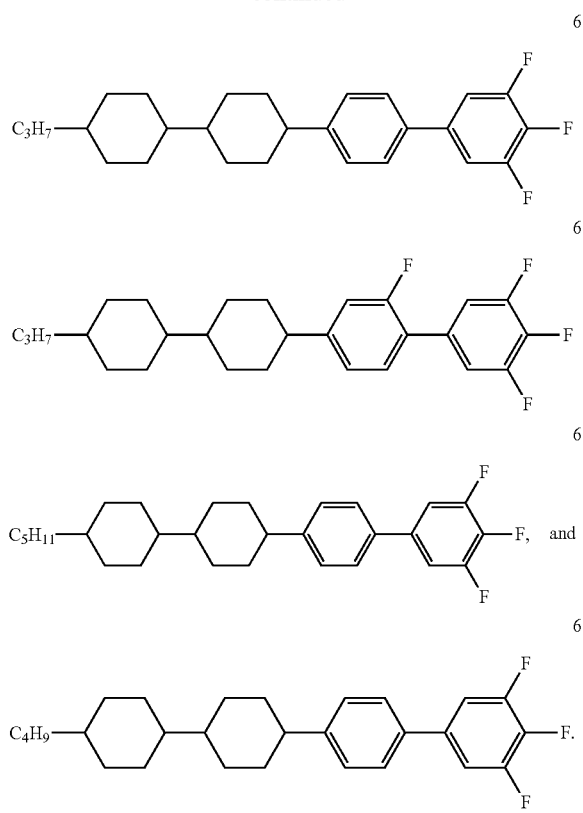

In addition, use of the compound of Formula I or the liquid crystal mixture according to the present invention in the preparation of a liquid crystal display material or electrooptical display material, and a liquid crystal display material or electrooptical display material containing the compound of Formula I or the liquid crystal mixture also fall within the protection scope of the present invention.

EXAMPLES

The present invention is further elaborated in connection with specific examples below; however, the present invention is not limited thereto. Unless specifically indicated otherwise, the processes are all conventional. Unless specifically indicated otherwise, the raw materials are all commercially available.

The compound of Formula I is prepared following a method as described in Synthesis Routes 1, 2, and 3 below. In Synthesis Route 2, the synthesis of some intermediates that are not commercially available is given, and the synthesis principles, operations, conventional post treatments, silica gel column chromatography, purification through recrystallization, and others are all known to persons of skill in the art. The target products can be absolutely obtained through the synthesis process described below.

The progression of the reaction process is generally monitored by TLC. The treatments after reaction generally include water washing, extracting, combining the organic phases and then drying, evaporating off the solvent under reduced pressure, recrystallizing, and column chromatography. The present invention may be accomplished by those skilled in the art following the description below.

Synthesis Route 1:

A compound of Formula I is prepared where

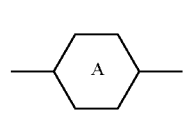

is 1,4-phenylene or 1,4-phenylene substituted with fluoro, m is 1 or 2 or 3, and n is 0 or 1; and

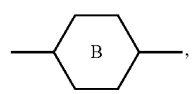

and $X_1$ to $X_5$ are as defined in Formula I.

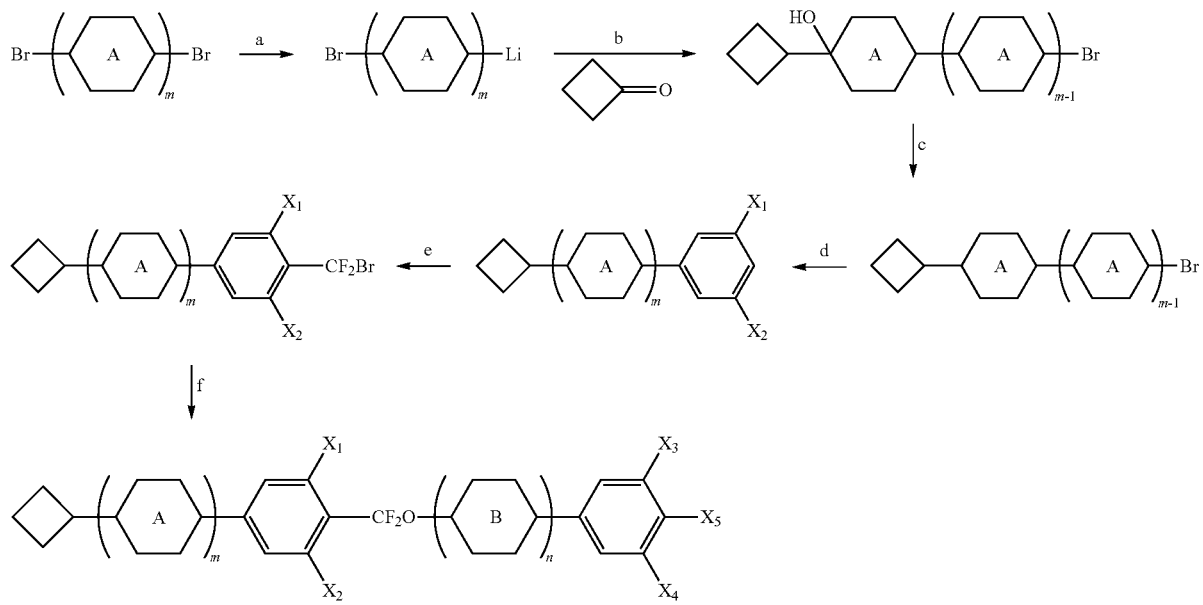

1) Under an inert atmosphere,

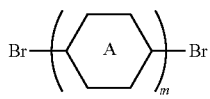

is dissolved in tetrahydrofuran and cooled to −70° C., then n-butyl lithium is added for exchanging halogen with lithium, and stirred for an additional 15 min after addition. Cyclobutanone

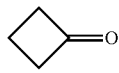

is added at this temperature to perform the addition reaction with the lithium reagent, during which the reaction system gradually becomes thin and completely clear after addition. The reaction solution is heated to 0° C. and poured into water. The organic layer is separated, extracted, washed with water, evaporated to completely remove the solvent, and recrystallized in ethanol, to obtain a white crystal

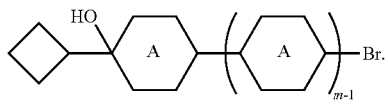

2) The

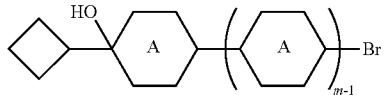

obtained in Step 1) is dissolved in dichloromethane, and cooled to −70° C. with stirring. Triethyl silicane ($SiH(C_2H_5)_3$) is added dropwise. Then boron trifluoride etherate ($BF_3 \cdot EtO_2$) is added dropwise to eliminate the hydroxyl group, whereby the solid is gradually dissolved. After addition, the solution is naturally warmed to −10° C. and poured into aqueous sodium carbonate. The organic phase is separated, extracted, washed with water, and purified by silica gel column chromatography, to obtain

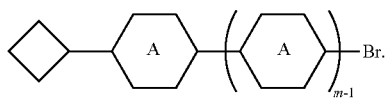

3)

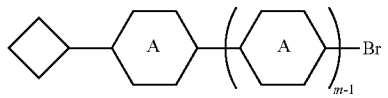

obtained in Step 2), phenylboronic acid

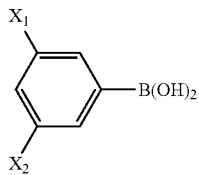

substituted with $X_1$ and $X_2$, toluene, ethanol, water, sodium carbonate and the catalyst tetrakis(triphenylphosphine)palladium are uniformly mixed and heated to reflux for SUZUKI reaction for 4 hrs. The reaction solution is poured into water. The organic phase is separated, extracted, washed with water, purified by silica gel column chromatography, concentrated, and recrystallized in ethanol, to obtain

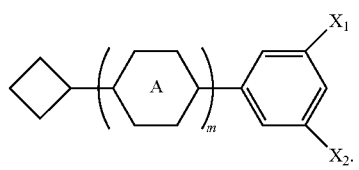

4)

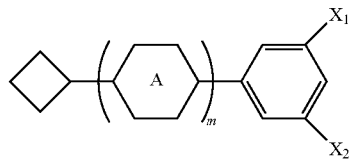

obtained in Step 3) is dissolved in tetrahydrofuran, purged with nitrogen, and cooled to −70° C. n-butyl lithium is added dropwise and a lithium reagent is obtained through substitution with lithium. After addition, a solution of difluorodibromomethane in tetrahydrofuran is added dropwise to replace lithium. The reaction solution is naturally warmed to 0° C., poured into water, and added with hydrochloric acid. The organic phase is separated, extracted, washed with water, and purified by silica gel column chromatography, to obtain a colorless liquid product containing

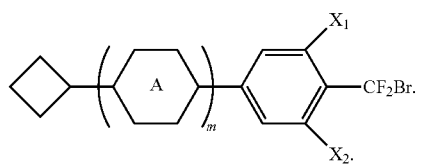

The product is directly used in next reaction step without separating by-products contained therein.

5)

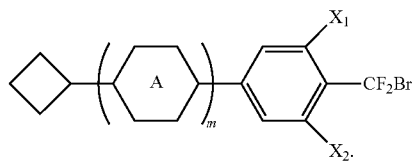

obtained in Step 4), dimethyl sulfoxide, anhydrous potassium carbonate, and

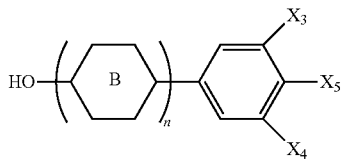

are uniformly mixed, subjected to etherification for 3 hrs at 60° C. with stirring, and poured into water to dissolve the inorganic salt. The organic phase is extracted, washed with water, purified by silica gel column chromatography, recrystallized 3 times in ethanol, and then recrystallized once in petroleum ether, to obtain a compound of Formula I in which

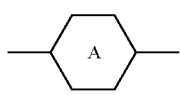

is 1,4-phenylene or 1,4-phenylene substituted with fluoro, m is 1 or 2 or 3, and n is 0 or 1.

Synthesis Route 2:

A compound of Formula I is prepared where

is 1,4-cyclohexylene, m is 1 or 2 or 3, n is 0 or 1, and

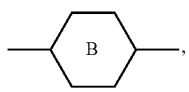

and $X_1$ to $X_5$ are as defined in Formula 1.

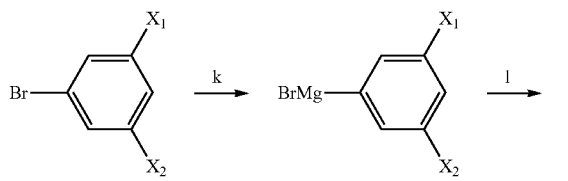

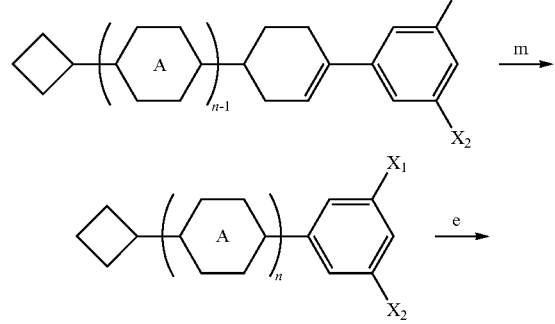

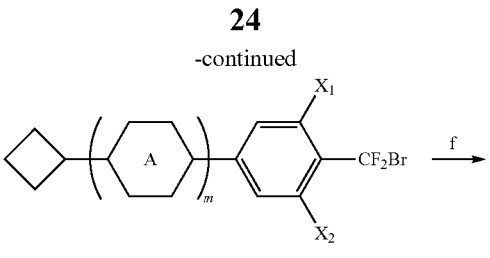

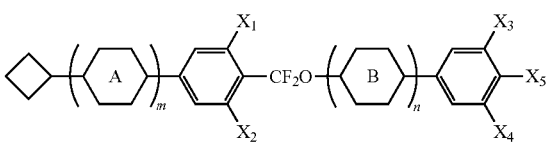

1)

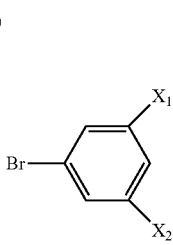

is dissolved in tetrahydrofuran. Magnesium powder and tetrahydrofuran are added to a three-neck flask and heated to reflux. For preparing a Grignard reagent, the solution above is added dropwise in a small amount, and kept to add dropwise under reflux after the reaction is initiated (if it is difficult to initiate the reaction, iodine or bromoethane is added for initiation), and refluxed for 1 hr after addition, to obtain the Grignard reagent

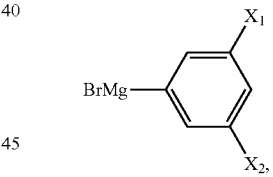

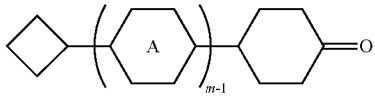

is added dropwise for addition reaction while cooling in a water bath, and refluxed for another 1 hr after addition, to obtain a sticky reaction solution. The reaction solution is poured into iced water and hydrochloric acid, and hydrolyzed with stirring. The organic phase is separated, extracted, washed with water, evaporated to completely remove the solvent, added with toluene and p-toluene sulfonic acid, and water is removed under reflux until no water is separated out after 3 hrs. Then, it is purified by silica gel column chromatography, to obtain a light yellow liquid. The liquid is evaporated to completely remove the solvent and recrystallized in ethanol, to obtain

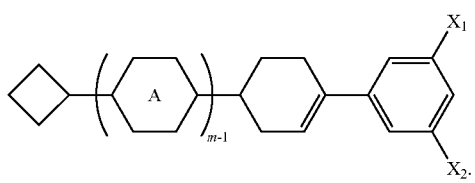

2)

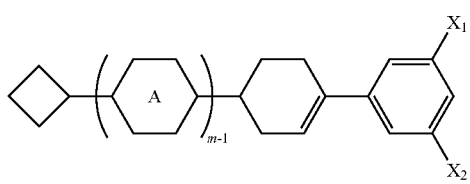

obtained in Step 1) is dissolved in ethanol and toluene, added with Pd/C, and hydrogenated for 6 hrs under normal pressure until the theoretical hydrogen absorption is attained. Then the Pd/C is filtered off, and the filtrate is evaporated under reduced pressure to remove the solvent, to obtain

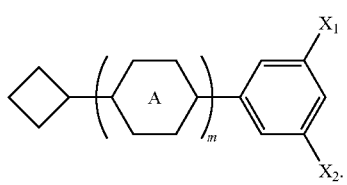

3)

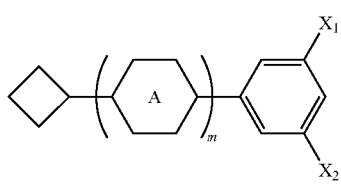

obtained in Step 2) is dissolved in tetrahydrofuran, purged with nitrogen, and cooled to −70° C. n-butyl lithium is added dropwise and a lithium reagent is obtained through substitution with lithium. After addition, a solution of difluorodibromomethane in tetrahydrofuran is added dropwise for addition reaction. The reaction solution is naturally warmed to 0° C., poured into water, and added with hydrochloric acid. The organic phase is separated, extracted, washed with water, purified by silica gel column chromatography, to obtain a colorless liquid product containing

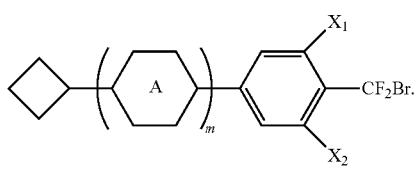

The product is directly used in next reaction step without separating by-products contained therein.

4)

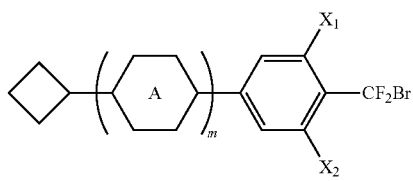

obtained in Step 3), dimethyl sulfoxide, anhydrous potassium carbonate, and

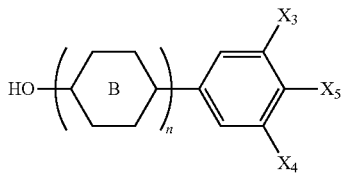

are uniformly mixed, subjected to etherification for 3 hrs at 60° C. with stirring, and poured into water to dissolve the inorganic salt. The organic phase is extracted, washed with water, purified by silica gel column chromatography, recrystallized 3 times in ethanol, and then recrystallized once in petroleum ether, to obtain a compound of Formula I in which

is 1,4-cyclohexylene, m is 1 or 2 or 3, and n is 0 or 1.

The synthesis route of the intermediate

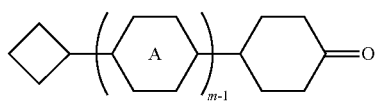

used in Step 1) is as follows.

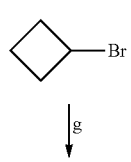

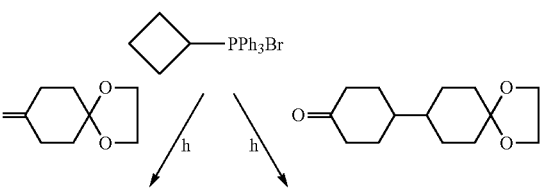

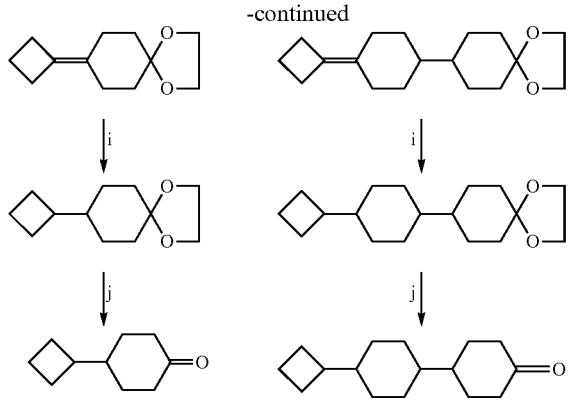

g: PPh₃, toluene, reflux
h: THF, potassium tert-butoxide, −10° C.,

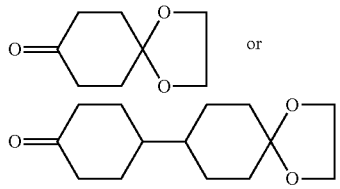

i: isopropanol, Pd/C, H₂
j: toluene, 85% formic acid

The synthesis process is specifically as follows. Bromocyclobutane and triphenylphosphine are directly heated to 100° C. for 6 hrs in the absence of a solvent, and part of the unreacted raw material is dissolved in toluene, to obtain cyclobutyl triphenylphosphonium bromide. The resulting cyclobutyl triphenylphosphonium bromide is reacted with potassium tert-butoxide in the solvent tetrahydrofuran at 0° C. to generate the corresponding Ylide reagent, which undergoes Witting reaction with

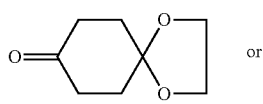

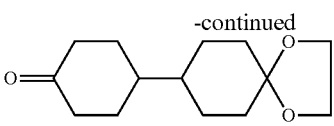

for 2-4 hrs. The solvent is directly removed by evaporation. The product intermediate alkene is extracted out with petroleum ether, which is hydrogenated in the solvent isopropanol in the presence of the catalyst Pd/C, with the alkene bond converted into a saturated bond. The trans-structured product is recovered through recrystallization in petroleum ether, and deprotected in the presence of formic acid in the solvent toluene at room temperature, to obtain

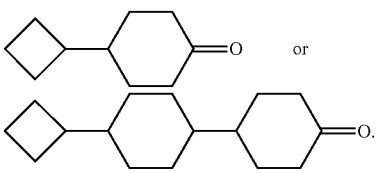

Synthesis Route 3:
A compound of Formula I is prepared where

is selected from at least one of 1,4-cyclohexylene, 1,4-phenylene and 1,4-phenylene substituted with fluoro, m is 2 or 3,

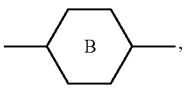

n, $X_1$ to $X_5$ are as defined in Formula I; and $X_6$ is selected from any one of H and F.

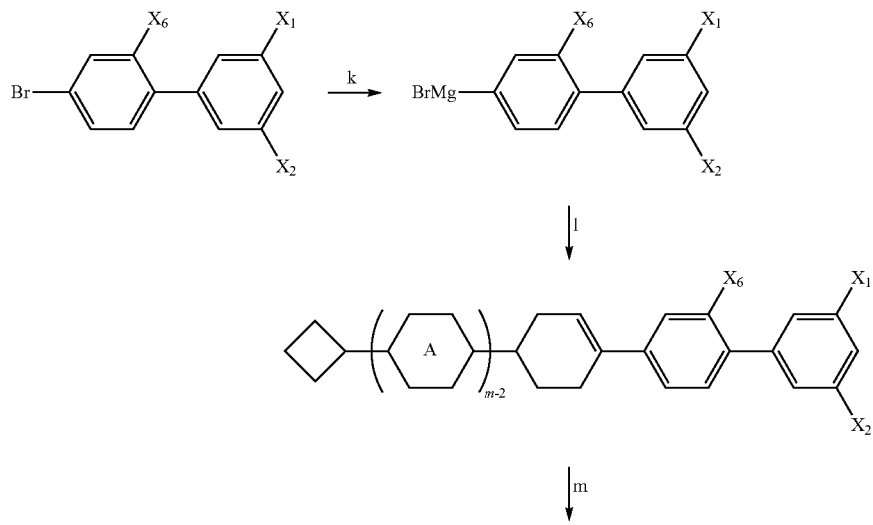

-continued

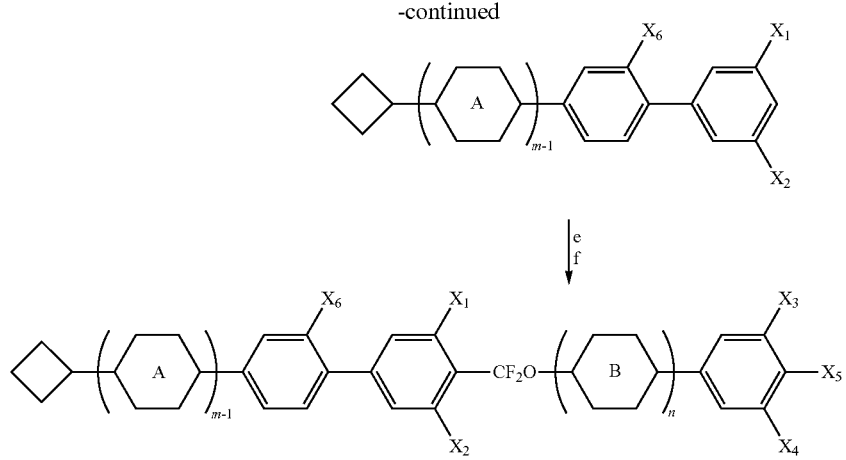

1)

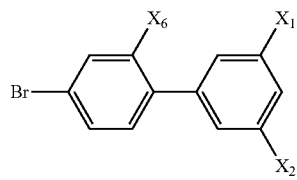

is dissolved in tetrahydrofuran. Magnesium powder and tetrahydrofuran are added to a three-neck flask and heated to reflux. For preparing a Grignard reagent, the solution above is added dropwise in a small amount, and kept to add dropwise under reflux after the reaction is initiated (if it is difficult to initiate the reaction, iodine or bromoethane is added for initiation), and refluxed for 1 hr after addition, to obtain the Grignard reagent

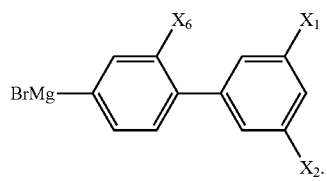

A solution of

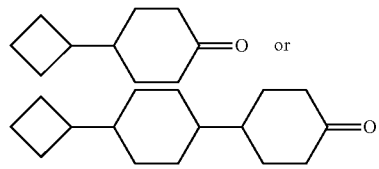

in tetrahydrofuran is added dropwise for addition reaction while in a water bath, and refluxed for another 1 hr after addition, to obtain a sticky reaction solution. The reaction solution is poured into iced water and hydrochloric acid, and hydrolyzed. The organic phase is separated, extracted, washed with water, evaporated to completely remove the solvent, added with toluene and p-toluene sulfonic acid, and water is removed under reflux until no water is separated out after 4 hrs. Then, it is purified by silica gel column chromatography, and recrystallized in a mixed solvent of toluene and ethanol to obtain

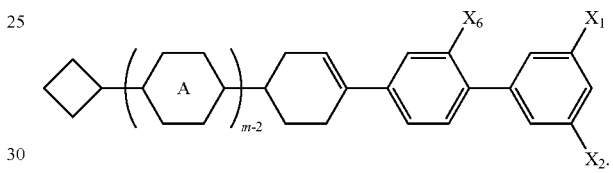

2)

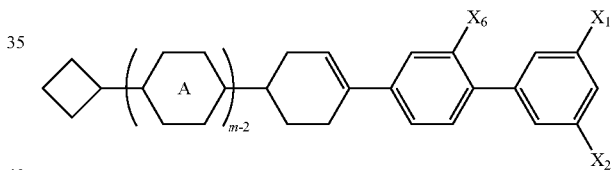

obtained in Step 1) is dissolved in ethanol and toluene, added with Pd/C, and hydrogenated for 6 hrs under normal pressure until the theoretical hydrogen absorption is attained. Then the Pd/C is filtered off, and the filtrate is evaporated under reduced pressure to remove the solvent, to obtain

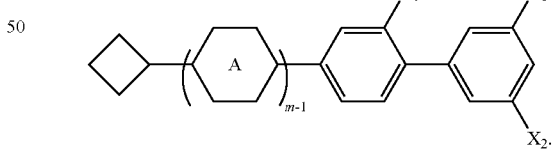

3)

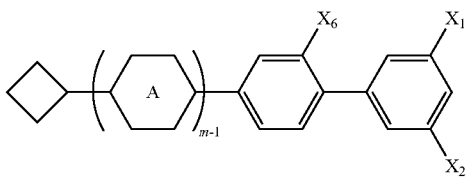

obtained in Step 2) is dissolved in tetrahydrofuran, purged with nitrogen, and cooled to −70° C. n-butyl lithium is added dropwise and a lithium reagent is obtained through substitution with lithium. After addition, a solution of difluorodibromomethane in tetrahydrofuran is added dropwise for substitution reaction. The reaction solution is naturally warmed to 0° C., poured into water, and added with hydrochloric acid. The organic phase is separated, extracted, washed with water, and purified by silica gel column chromatography, to obtain a colorless liquid product containing

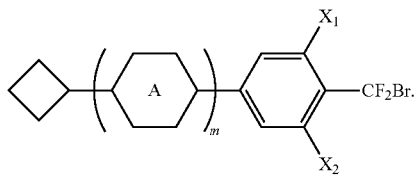

The product is directly used in next reaction step without separating by-products contained therein.

4)

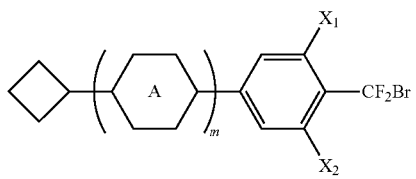

obtained in Step 3), dimethyl sulfoxide, anhydrous potassium carbonate, and

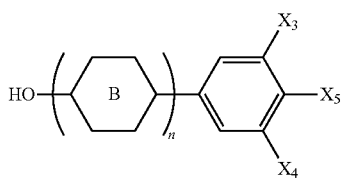

are uniformly mixed, subjected to etherification for 3 hrs at 60° C. with stirring, and poured into water to dissolve the inorganic salt. The organic phase is extracted, washed with water, purified by silica gel column chromatography, recrystallized 3 times in ethanol, and then recrystallized once in petroleum ether, to obtain a compound of Formula I in which

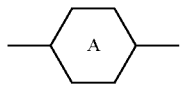

is selected from any one of 1,4-cyclohexylene, 1,4-phenylene and 1,4-phenylene substituted with fluoro, and m is 2 or 3.

In the examples below, GC represents gas chromatographic purity, MP represents melting point, MS represents mass spectrometry, Δ∈ represents dielectric anisotropy, Δn represents optical anisotropy, and $\gamma_1$ represents rotary viscosity.

Contrast is a ratio of the light intensities at bright and black states of a liquid crystal display, and determined as follows. The liquid crystals are filled in a liquid crystal cell, and a polarizer is attached. The driving voltage is determined in a normal white mode according to the threshold voltage of the liquid crystals. Then wire is led out from the attached liquid crystal cell, and testing is performed in constant backlight. The contrast is a ratio of the light intensities at light and black states determined for the liquid crystal cell without or with a voltage applied.

Variation of contrast at normal temperature vs. low temperature (%)=(contrast at normal temperature−contrast at low temperature)/contrast at normal temperature×100(%), in which the normal temperature is 25° C. and the low temperature is −20° C.

Cp represents clearing point. The clearing point may be directly determined, and for a compound for which the clearing point cannot be directly determined, fitted data is calculated following the method below.

In the formulation of a mixed liquid crystal, numerous suitable monomer liquid crystals may be mixed, to form an eutectic mixture, thereby effectively lowering the melting point of the mixed liquid crystal. In addition, a monomer liquid crystal with a high clearing point may be added to increase the clearing point of the mixed liquid crystal, thereby formulating a mixed liquid crystal with a nematic phase over a satisfactory temperature range. The clearing point of the mixed liquid crystal, and the clearing points and contents of the monomer liquid crystals meet the following relationship:

$$Tc = \Sigma X_i T_i$$

where, Tc represents the clearing point of the mixed liquid crystal, $X_i$ represents the content of the monomer liquid crystals present in the mixed liquid crystal, and $T_i$ represents the clearing point of the monomer liquid crystals.

Based on this, in case that the concentration of all monomer liquid crystals in the mixed liquid crystal, and the clearing points of other monomer liquid crystals are known, the clearing point of an monomer liquid crystal unknown in the examples below may be calculated following the equation above. In the mixed liquid crystal, the content of the component to be determined is 10 parts by weight, and the contents of other liquid crystal monomers are 100 parts in total. Specific composition and amounts in parts by weight are shown below:

25

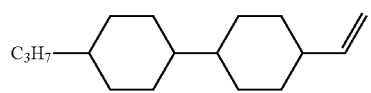

11

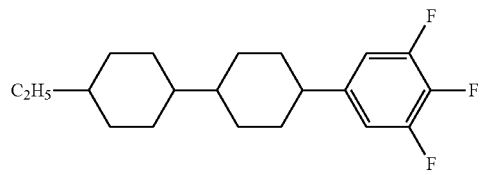

11

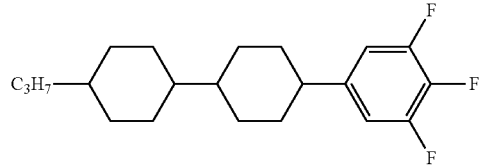

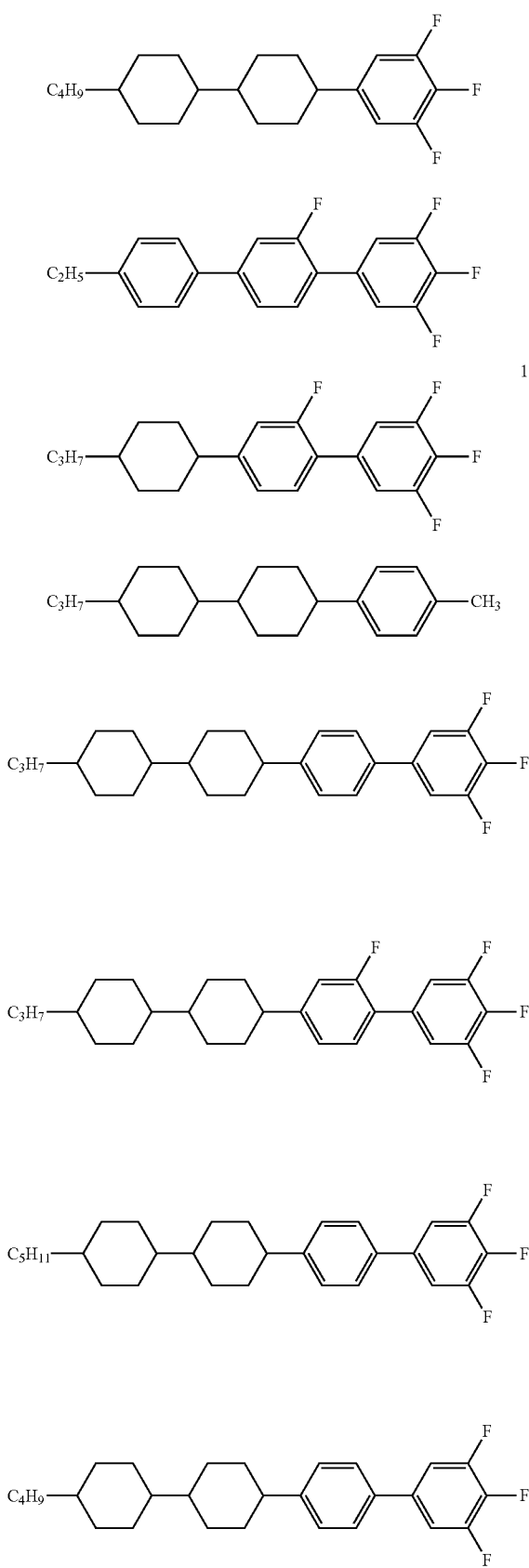

Example 1

Preparation of Compounds of Formulas I2 and I6

Step 1:

47.2 g (0.2 mol) p-dibromobenzene was dissolved in 280 ml tetrahydrofuran, and cooled to −70° C. under nitrogen atmosphere, during which the reaction solution became sticky. 84 ml (0.21 mol, 2.5M) n-butyl lithium was added dropwise for exchanging bromine with lithium, and stirred for an additional 15 min after addition. 14 g (0.2 mol) cyclobutanone was added at this temperature to perform the addition reaction with the lithium reagent, during which the reaction system gradually became thin and completely clear after addition. The reaction solution was heated to 0° C. and poured into 300 ml water. The organic layer is separated, extracted, washed with water, evaporated to completely remove the solvent, and recrystallized in ethanol, to obtain 25 g of a white crystal (1-a). Yield: 60%.

Step 2:

13 g (0.057 mol) (1-a) was dissolved in 130 ml dichloromethane, and cooled to −70° C. with stirring. 15 g (0.132 mol) triethyl silicane was added dropwise. Then, 19 g (0.132 mol) boron trifluoride etherate was added dropwise to eliminate the hydroxyl group, whereby the solid was gradually dissolved. After addition, the solution was naturally warmed to −10° C. and poured into 100 ml aqueous sodium carbonate. The organic phase is separated, extracted, washed with water, and purified by silica gel column chromatography, to obtain 12 g of a colorless liquid (1-b) in a quantitative yield.

Step 3:

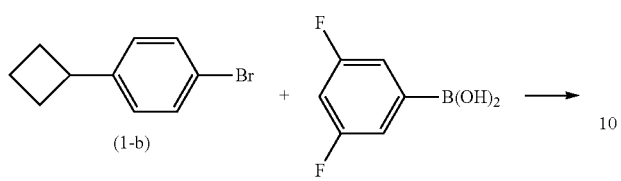

(1-b)

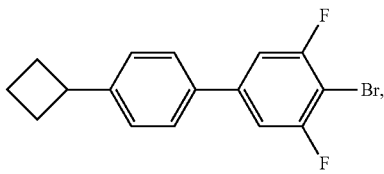 [SMILES: Fc1cc(-c2ccc(C3CCC3)cc2)cc(F)c1Br]

(1-c)

14 g (0.066 mol) (1-b), 11.5 g (0.073 mol) 3,5-difluorophenylboronic acid, 50 ml toluene, 50 ml ethanol, 50 ml water, 8.5 g (0.08 mol) sodium carbonate, and 0.4 g tetrakis(triphenylphosphine)palladium were heated together to reflux for SUZUKI reaction for 4 hrs. The reaction solution was poured into 100 ml water. The organic phase was separated, extracted, washed with water, purified by silica gel column chromatography, concentrated, and recrystallized in 50 ml ethanol, to obtain 7.8 g (1-c). Yield: 48%.

Step 4:

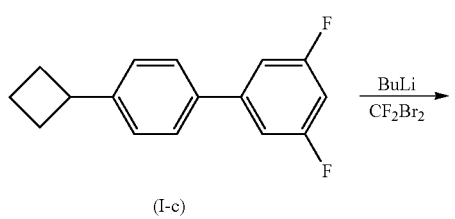

(I-c)

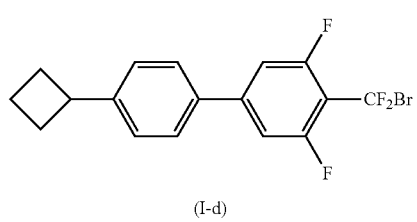

(I-d)

7.8 g (0.032 mol) (1-c) was dissolved in 80 ml tetrahydrofuran, purged with nitrogen, and then cooled to −70° C. 16 ml (0.040 mol, 2.5 M) n-butyl lithium was added dropwise for substitution with lithium. After addition, a solution of 10.5 g (0.050 mol) difluorodibromomethane in 10 ml tetrahydrofuran was added dropwise for addition reaction. The reaction solution was naturally warmed to 0° C., poured into 100 ml water, and added with 1 ml hydrochloric acid. The organic phase is separated, extracted, washed with water, and purified by silica gel column chromatography, to obtain 10.5 g of a colorless liquid product (1-d). As shown by GC, the product contains 73.9% of (1-d) and 23.6% of

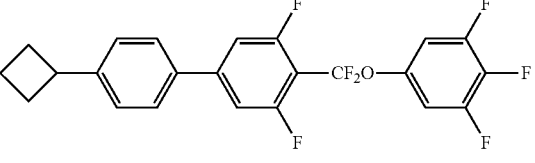

and is directly used in nest reaction step without further purification.

Step 5:

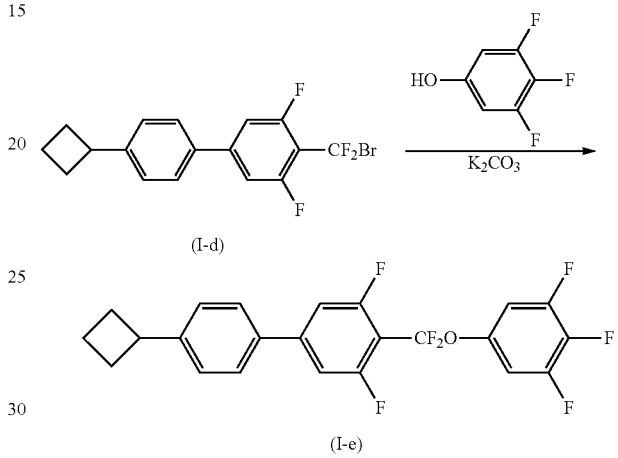

(I-d)

(I-e)

10.5 g (0.021 mol) (1-d) obtained in Step 4, 50 ml dimethyl sulfoxide, 7.7 g anhydrous potassium carbonate, and 3.7 g (0.025 mol) 3,4,5-trifluorophenol were reacted for 3 hrs at 60° C. with stirring, then poured into 200 ml water to dissolve the inorganic salt, extracted, washed with water, purified by silica gel column chromatography, recrystallized 3 times in ethanol, and then recrystallized once in petroleum ether, to obtain 5.0 g of a product (1-e) with a purity of 99.9%. MP: 37.4° C. MS: see FIG. 1.

It can be known from above that the product has a correct structure, and is a compound of Formula I2.

Detection results for liquid crystal performances of the compound: Δn [589 nm, 20° C.]: 0.136; Δ∈ [KHz, 20° C.]: 16.1; Cp: fitted data 0° C.

Following the steps above except that p-dibromobenzene in Step 1) was replaced by

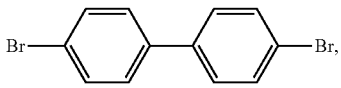 [SMILES: Brc1ccc(-c2ccc(Br)cc2)cc1]

to obtain a compound of Formula I below:

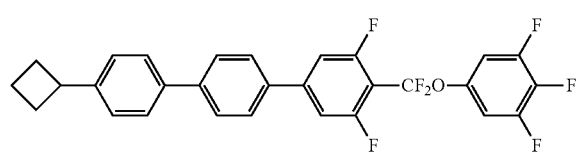

Detection results for liquid crystal performances of the compound: MP: 120° C.; Δn [589 nm, 20'C]: 0.211; Δ∈ [KHz, 20° C.]: 17.5; Cp: 130° C.

Example 2

Preparation of Compound of Formula I1

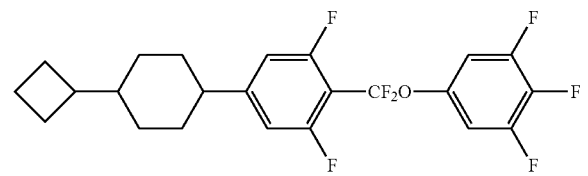

Step 1:

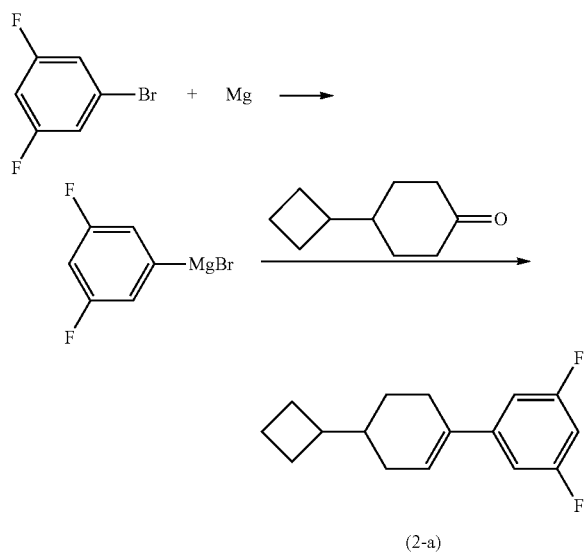

67.2 g (0.35 mol) 3,5-difluorophenyl bromide was dissolved in 100 ml tetrahydrofuran for use. 8.4 g (0.35 mol) magnesium powder and 100 ml tetrahydrofuran were added to a 500 ml three-neck flask and heated to reflux. For preparing a Grignard reagent, the solution above was added dropwise in a small amount, and kept to add dropwise under reflux after the reaction was initiated (if it was difficult to initiate the reaction, iodine or bromoethane was added for initiation), and refluxed for 1 hr after addition, to obtain the Grignard reagent 3,5-difluorophenyl bromide. 53.2 g (0.35 mol) 4-cyclobutylcyclohexanone was added dropwise for addition reaction while cooling in a water bath, and refluxed for another 1 hr after addition, to obtain a sticky reaction solution. The reaction solution was poured into 300 ml iced water and 30 ml hydrochloric acid, and hydrolyzed with stirring. The organic phase was separated, extracted, washed with water, evaporated to completely remove the solvent, added with 150 ml toluene and 1 g p-toluene sulfonic acid, and water was removed under reflux until no water was separated out after about 3 hrs. Then, it was purified by silica gel column chromatography, to obtain a light yellow liquid. The liquid was evaporated to completely remove the solvent and recrystallized in ethanol, to obtain 52 g of a product (2-a). Yield: 60%.

Step 2:

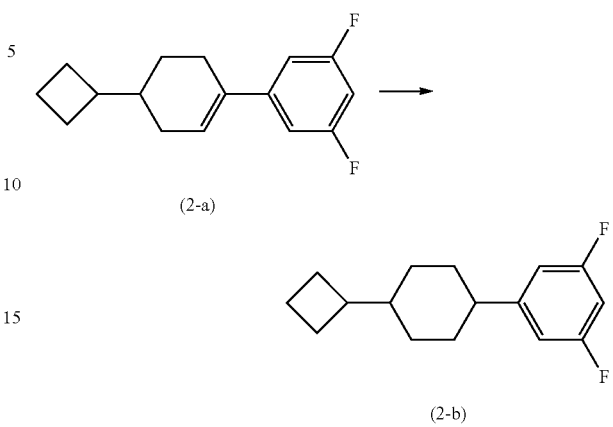

52 g of the product (2-a) obtained in Step 1 was dissolved in 200 ml ethanol and 100 ml toluene, added with 2 g Pd/C, and hydrogenated for 6 hrs under normal pressure until the theoretical hydrogen absorption was attained. Then the Pd/C was filtered off, and the filtrate was evaporated under reduced pressure to remove the solvent, to obtain 52 g of a colorless liquid (2-b).

Step 3: Following the operations in Step 4 of Example 1,

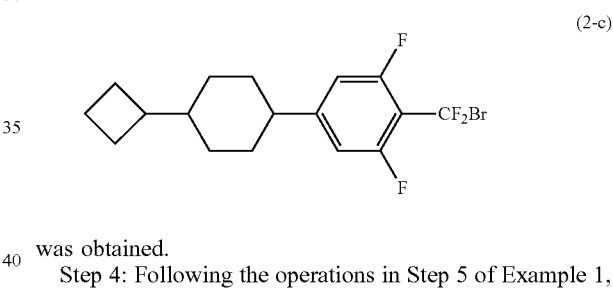

was obtained.

Step 4: Following the operations in Step 5 of Example 1,

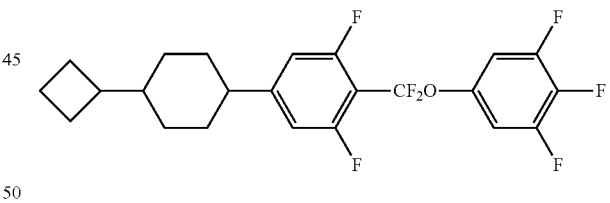

was obtained.

MP: 39.5° C.; Δn [589 nm, 20° C.]: 0.06; Δ∈ [KHz, 20° C.]: 14.6.

Example 3

Preparation of Compound of Formula I8

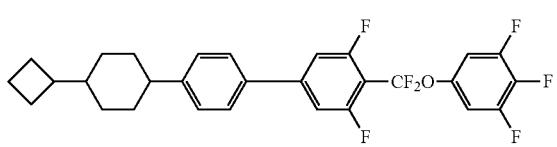

Step 1:

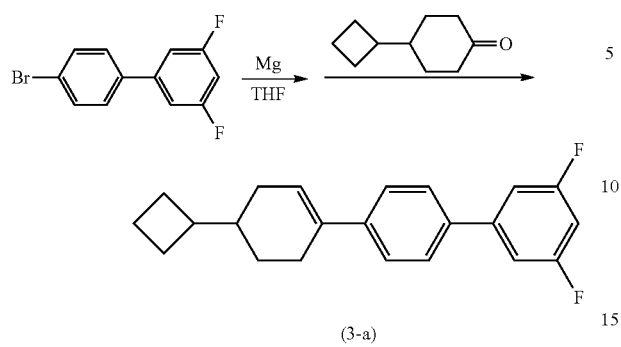

(3-a)

40.3 g (0.15 mol) 4-bromo-3',5'-difluorobiphenyl was dissolved in 50 ml tetrahydrofuran for use. 3.6 g (0.15 mol) magnesium powder and 50 ml tetrahydrofuran were added to a 500 ml three-neck flask and heated to reflux. For preparing a Grignard reagent, the solution above was added dropwise under reflux in a small amount, and kept to add dropwise under reflux after the reaction was initiated (if it was difficult to initiate the reaction, iodine or bromoethane was added for initiation), and refluxed for 0.5 hr after addition. A solution of 22.8 g (0.15 mol) 4-cyclobutylcyclohexanone in 30 ml tetrahydrofuran was added dropwise while in a water bath, and then refluxed for another 1 hr for addition reaction. A sticky liquid was obtained, which was poured into 200 mil iced water and 15 ml hydrochloric acid and hydrolyzed. The organic phase was separated, extracted, washed with water, evaporated to completely remove the solvent, added with 200 ml toluene and 1 g p-toluene sulfonic acid, and water was removed under reflux until no water was separated out after 4 hrs. Then, it was purified by silica gel column chromatography, and recrystallized in a mixed solvent of toluene and ethanol, to obtain 24.6 g of a white crystal (3-a). Yield: 50%.

Step 2:

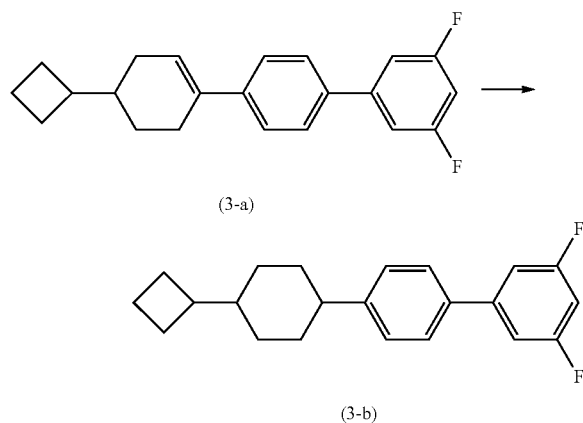

24.6 g (3-a) was dissolved in 200 ml toluene and 50 ml ethanol, added with 1 g Pd/C, and hydrogenated for 5 hrs under normal pressure until the theoretical hydrogen absorption was attained. Then the Pd/C was filtered off, and the filtrate was concentrated. The residue was recrystallized in a mixed solvent of toluene and ethanol to obtain 22 g of a white crystal (3-b). Yield: 90%.

Step 3: Following the operations in Step 4 of Example 1,

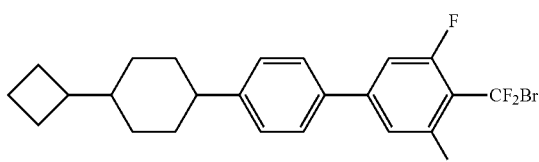

was obtained.

Step 4: Following the operations in Step 5 of Example 1,

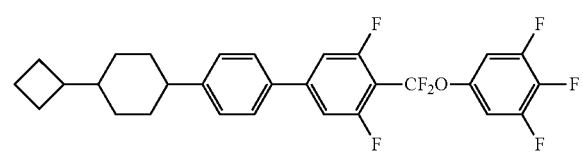

was obtained.

MP; 115° C.; Δn [589 nm, 20° C.]: 0.14; Δ∈ [KHz, 20° C.]: 15.6; Cp: fitted data 91° C.

Example 4

Preparation of Liquid Crystal Mixture a

The component A, component B and component C are uniformly mixed, to obtain a liquid crystal mixture a. The component A is the component of Formula I2 prepared in Example 1:

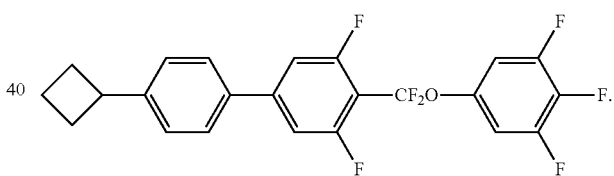

The component B is the compound of Formula II1:

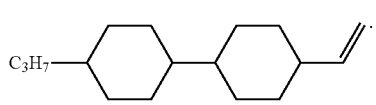

The component C is a mixture consisting of the compounds of Formula III below, in parts by weight:
compound of Formula III2:

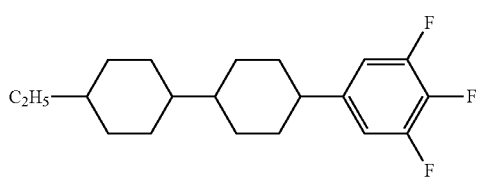

compound of Formula III2:

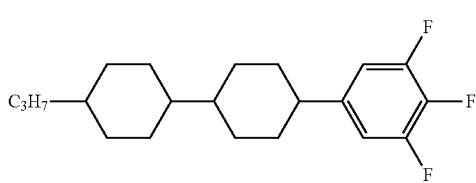

compound of Formula III2:

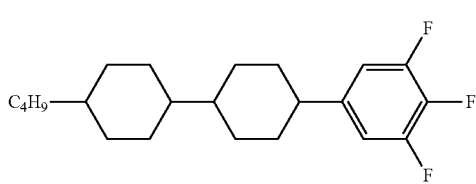

compound of Formula III5:

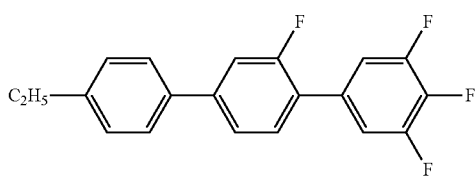

compound of Formula III4:

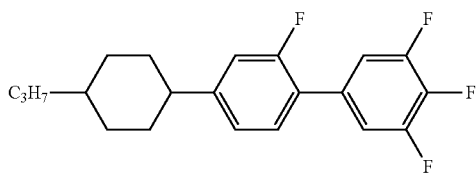

compound of Formula III9:

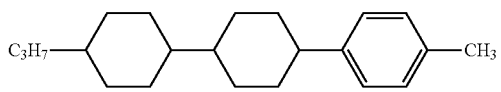

compound of Formula III6:

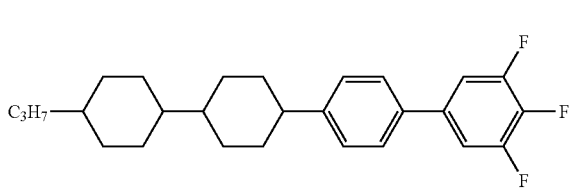

compound of Formula III7:

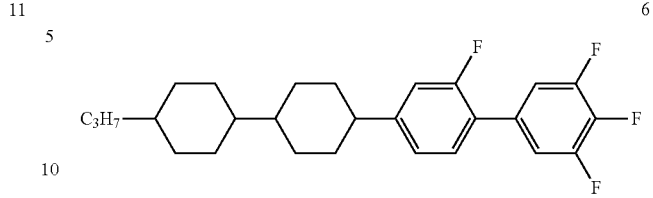

compound of Formula III7:

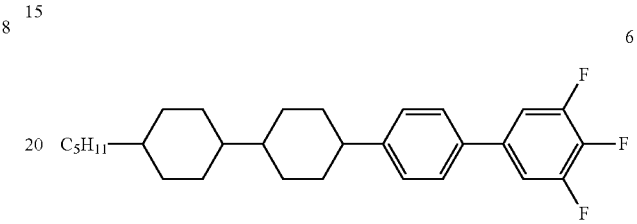

compound of Formula III7:

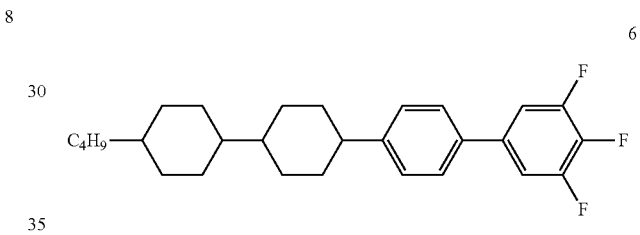

The weight ratio of the component A, B and C is 10:25:75.

Detection results for liquid crystal performances of a liquid crystal mixture consisting of the components B and C (i.e. liquid crystal mixture M1) are shown below: Δn [589 nm, 25° C.]: 0.100; Δ∈ [1 KHz, 25° C.]: 10.6; Cp: 95° C.; $\gamma_1$ [25° C.]: 130 mPa·s; contrast at normal temperature: 333, contrast at low temperature: 216, variation (%): 35%.

Detection results for liquid crystal performances of the liquid crystal mixture a are shown below: Δn [589 nm, 25° C.]: 0.1036; Δ∈ [1 KHz, 25° C.]: 11.5; Cp: 86° C.: $\gamma_1$ [25° C.]: 120.5 mPa·s; contrast at normal temperature: 387, contrast at low temperature: 318, variation (%): 18%.

Example 5

Preparation of Liquid Crystal Mixture b

Following the method in Example 4, except that the component A was replaced by equivalent parts by weight of the compound of Formula I1 prepared in Example 2:

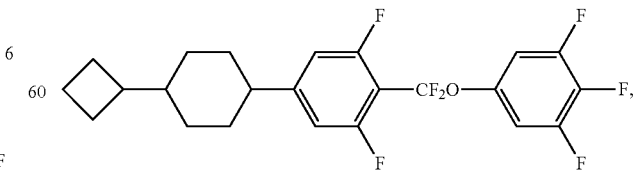

to obtain a liquid crystal mixture b.

Detection results for liquid crystal performances of the liquid crystal mixture b: Δn [589 nm, 25° C.]: 0.1035; Δ∈ [1

KHz, 25° C.]: 10.9; Cp: 83'C; $\gamma_1$ [25° C.]: 123 mPa·s; contrast at normal temperature: 359, contrast at low temperature: 284, variation (%): 21%.

Example 6

Preparation of Liquid Crystal Mixture c

Following the method in Example 4, except that the component A was replaced by equivalent parts by weight of the compound of Formula 18 prepared in Example 3:

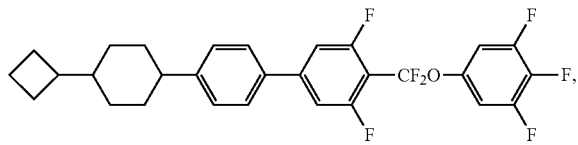

to obtain a liquid crystal mixture c.

Detection results for liquid crystal performances of the liquid crystal mixture c: Δn [589 nm, 25° C.]: 0.1040; Δ∈ [1 KHz, 25° C.]: 11.1; Cp: 95° C.; $\gamma_1$ [25° C.]: 126 mPa·s; contrast at normal temperature: 369, contrast at low temperature: 294, variation (%): 20%.

Example 7

Preparation of Liquid Crystal Mixture d

Following the method in Example 4, except that the component A was replaced by 5 parts by weight of the compound of Formula I6 prepared in Example 1:

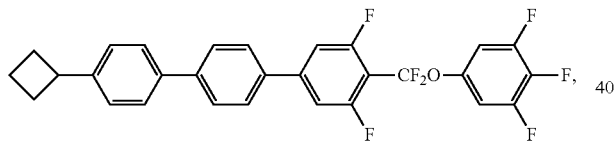

to obtain a liquid crystal mixture d.

Detection results for liquid crystal performances of the liquid crystal mixture d: Δn [589 nm, 25° C.]: 0.1055; Δ∈ [1 KHz, 25° C.]: 11.1; Cp: 96.3° C.; $\gamma_1$ [25° C.]: 123 mPa·s; contrast at normal temperature: 364, contrast at low temperature: 271, variation (%): 25%.

It can be seen from Examples 4-7 that addition of the compound of Formula I to the mixture has the advantages of increasing the dielectric anisotropy Δ∈, decreasing the rotary viscosity $\gamma_1$, and lowering the variation in contrast from normal to low temperature of the mixture.

INDUSTRIAL APPLICABILITY

Because the response speed t, the thickness d of the liquid crystal cell, and the rotary viscosity $\gamma_1$ of the liquid crystal meet the relationship: $t \propto \gamma_1 d^2$, a liquid crystal with a low rotary viscosity $\gamma_1$ has a short response time. The liquid crystal compound containing cyclobutyl as a terminal group and difluoromethyleneoxy (—CF$_2$O—) as a linking group in the molecular structure of the compound of Formula I according to the present invention, has not only a high dielectric anisotropy Δ∈, but also importantly a fast response speed t, a low rotary viscosity $\gamma_1$ and good performances at low temperature, which are of great significance for the formulation of a liquid crystal mixture.

What is claimed is:

1. A compound of Formula I

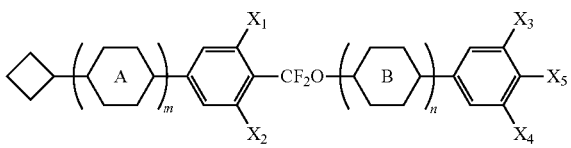

wherein

is selected from 1,4-cyclohexylene, 1,4-cyclohexylene in which one —CH$_2$— is substituted with O, 1,4-phenylene and 1,4-phenylene substituted with fluoro;

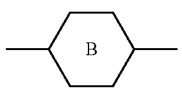

is selected from 1,4-phenylene and 1,4-phenylene substituted with fluoro;

X$_1$, X$_2$, X$_3$ and X$_4$ are each independently selected from H and F;

X$_5$ is selected from H, F, Cl, CF$_3$, CHF$_2$, OCF$_3$ and OCHF$_2$;

m is selected from 1, 2 and 3; and n is selected from 0 and 1.

2. The compound according to claim 1, characterized in that the compound of Formula I is any one of compounds of Formulas I1 to I18:

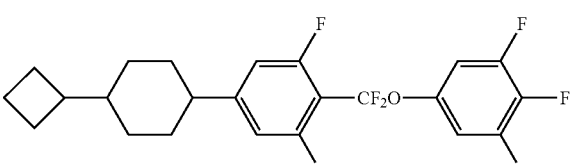

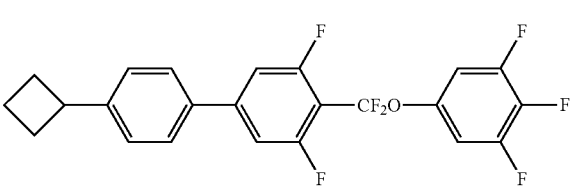

3. A liquid crystal mixture comprising a component A, wherein the component A consists of at least one of the compounds of Formula I according to claim 1.

4. The liquid crystal mixture according to claim 3, further comprising a component B and a component C;
   wherein the component B consists of at least one of the compounds of Formula II;
   the component C consists of at least one of the compounds of Formula III;

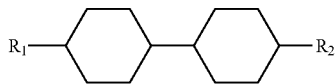

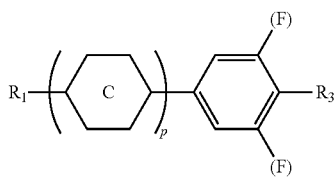

in Formulas II and III, $R_1$ and $R_2$ are each a C1-C6 alkyl or C2-C6 alkenyl;
$R_3$ is hydrogen, fluoro or C1-C6 alkyl;

is selected from 1,4-cyclohexylene, 1,4-phenylene and 1,4-phenylene substituted with fluoro;
p is 2 or 3; and
(F) is H or F; and
the weight ratio of the component A, component B and component C is 1-40:5-40:5-80 respectively.

5. The liquid crystal mixture according to claim 4, characterized in that the compound of Formula II is any one of the compounds having a structural formula below:

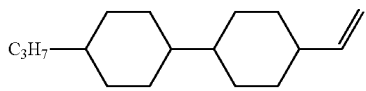

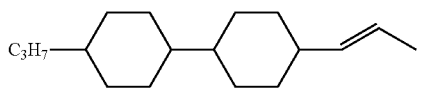

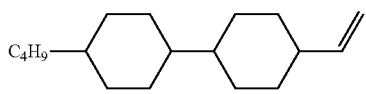

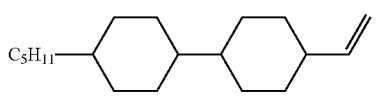

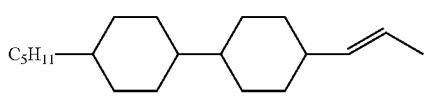

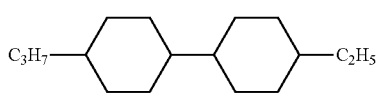

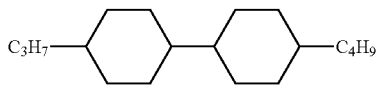

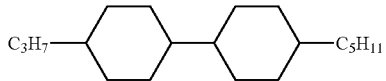

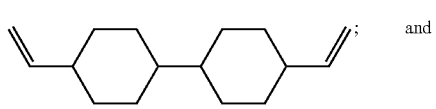

the compound of Formula III is any one of the compounds of Formulas III1 to III8:

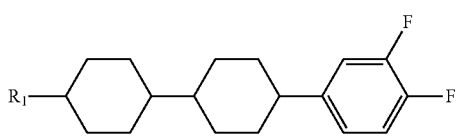

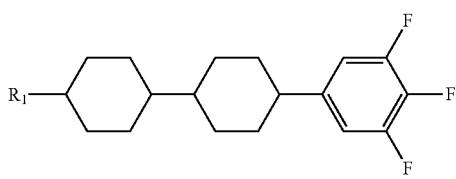

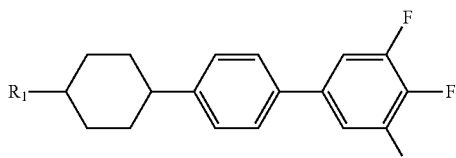

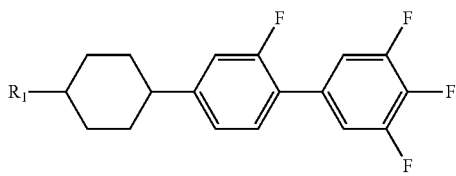

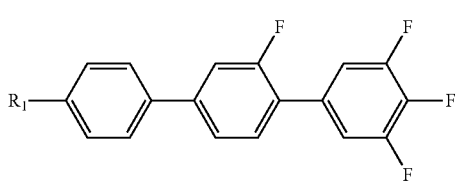

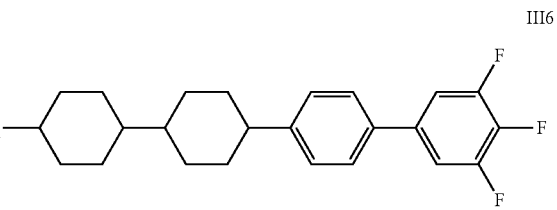

-continued

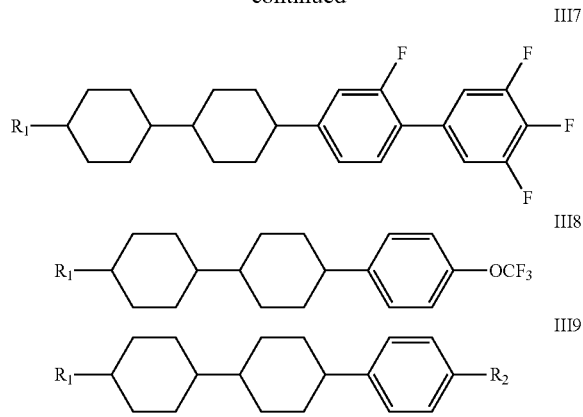

wherein $R_1$ is a C1-C6 alkyl or C2-C6 alkenyl.

6. The liquid crystal mixture according to claim 4, characterized in that in the component B, the compounds of Formula II are each present in an amount of 10-35% by weight of the total weight of the liquid crystal mixture; and
in the component C, the compounds of Formula III are each present in an amount of 2-12% by weight of the total weight of the liquid crystal mixture.

7. A liquid crystal display material comprising the compound of Formula I according to claim 1.

8. An electrooptical display material comprising the liquid crystal mixture according to claim 3.

9. The liquid crystal mixture according to claim 3, wherein the weight ratio of the component A, component B and component C is 10-35:15-35:25-75 respectively.

10. The liquid crystal mixture according to claim 3, wherein the weight ratio of the component A, component B and component C is 10:25:75 respectively.

* * * * *